United States Patent
Hubbell et al.

(10) Patent No.: US 6,465,001 B1
(45) Date of Patent: *Oct. 15, 2002

(54) TREATING MEDICAL CONDITIONS BY POLYMERIZING MACROMERS TO FORM POLYMERIC MATERIALS

(75) Inventors: Jeffrey A. Hubbell, Zumikon (CH); Chandrashekhar P. Pathak, Austin, TX (US); Amarpreet Sawhney, Bedford, MA (US); Neil Desai, Los Angeles, CA (US); Syed Hossainy, Edison, NJ (US); Jennifer L. Hill-West, Pearland, TX (US)

(73) Assignee: Board of Regents, The University of Texas Systems, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/033,871

(22) Filed: Mar. 3, 1998

Related U.S. Application Data

(60) Continuation of application No. 08/467,693, filed on Jun. 6, 1995, now Pat. No. 5,834,274, which is a division of application No. 08/024,657, filed on Mar. 1, 1993, now Pat. No. 5,573,934, which is a continuation-in-part of application No. 07/958,870, filed on Oct. 7, 1992, now Pat. No. 5,529,914, which is a continuation-in-part of application No. 07/870,540, filed on Apr. 20, 1992, now abandoned, which is a continuation-in-part of application No. 08/475,175, filed on Jun. 7, 1995, now Pat. No. 5,846,530, which is a division of application No. 08/232,054, filed on Apr. 28, 1994, now Pat. No. 5,837,747.

(51) Int. Cl.$^7$ ............... A61F 2/00; C12N 11/04; A61K 38/00; A61K 9/14; A61K 31/74

(52) U.S. Cl. ............ 424/423; 424/422; 424/484; 424/486; 424/487; 424/488; 424/78.08; 424/78.31; 424/93.1; 424/93.7; 424/94.1; 424/426; 435/197; 435/178; 435/180; 435/182; 435/382; 435/395; 514/2; 530/812; 530/813; 530/815; 530/817

(58) Field of Search ............... 424/93.7, 422, 424/423, 426, 484, 486, 487, 488, 78.08, 78.31, 93.1, 94.1; 435/177, 178, 180, 182, 395, 396, 402, 382; 514/2; 530/812, 813, 815, 817

(56) References Cited

U.S. PATENT DOCUMENTS

| | | |
|---|---|---|
| 3,960,150 A | 6/1976 | Hussain et al. ............ 424/428 |
| 3,981,303 A | 9/1976 | Higuchi et al. ............ 424/428 |
| 3,986,510 A | 10/1976 | Higuchi et al. ............ 424/428 |
| 3,993,071 A | 11/1976 | Higuchi et al. ............ 424/428 |
| 4,076,800 A | 2/1978 | Marsh et al. ............ 424/70.14 |
| 4,193,845 A | 3/1980 | Kaetsu et al. ............ 435/182 |
| 4,194,066 A | 3/1980 | Kaetsu et al. ............ 435/182 |
| 4,195,129 A | 3/1980 | Fukui et al. ............ 435/182 |
| 4,226,938 A | 10/1980 | Yoshida et al. ............ 435/176 |
| 4,272,617 A | 6/1981 | Kaetsu et al. ............ 435/82 |
| 4,283,325 A | 8/1981 | Berthet et al. ............ 424/630 |
| 4,295,762 A | 10/1981 | Slovinsky ............ 405/264 |
| 4,298,002 A | 11/1981 | Ronel et al. ............ 128/260 |
| 4,321,117 A | 3/1982 | Kaetsu et al. ............ 522/15 |
| 4,329,332 A | 5/1982 | Courvreur et al. ............ 424/1.25 |
| 4,359,483 A | 11/1982 | Kaetsu et al. ............ 427/2 |
| 4,376,059 A | 3/1983 | Davis et al. ............ 424/499 |
| 4,411,754 A | 10/1983 | Kaetsu et al. ............ 204/159.15 |
| 4,434,150 A | 2/1984 | Azad et al. | 
| 4,450,150 A | 5/1984 | Sidman ............ 424/424 |
| 4,511,478 A | 4/1985 | Nowinski et al. ............ 210/691 |
| 4,526,938 A | 7/1985 | Churchill et al. ............ 525/415 |
| 4,563,489 A | 1/1986 | Urist ............ 514/21 |
| 4,590,068 A | 5/1986 | Berthet et al. ............ 424/81 |
| 4,605,622 A | 8/1986 | Hasegawa et al. ............ 435/182 |
| 4,637,931 A | 1/1987 | Schmitz ............ 424/426 |
| 4,647,536 A | 3/1987 | Mosbach et al. ............ 435/177 |

(List continued on next page.)

FOREIGN PATENT DOCUMENTS

| | | |
|---|---|---|
| EP | 0 195 304 A | 9/1986 |
| WO | WO 91/10425 | 1/1991 |
| WO | WO 93/21266 | 4/1992 |
| WO | WO 93/09176 | 5/1993 |
| WO | WO 93/17669 | 9/1993 |

OTHER PUBLICATIONS

Altman, et al., "Long–Term Plasma Glucose Normalization in Experimental Diabetic Rats with Microencapsulated Implants of Benign Human Insulinomas," *Diabetes* 35:625–633 (year).

Amudeswari, et al., "Short–term biocompatability studies of hydrogel–grafted collagen copolymers," *J. Biomed. Materials Res.* 20:1103–1109 (1986).

(List continued on next page.)

*Primary Examiner*—David M. Naff
(74) *Attorney, Agent, or Firm*—Holland & Knight LLP

(57) ABSTRACT

Water soluble macromers are modified by addition of free radical polymerizable groups, such as those containing a carbon-carbon double or triple bond, which can be polymerized under mild conditions to encapsulate tissues, cells, or biologically active materials. The polymeric materials are particularly useful as tissue adhesives, coatings for tissue lumens including blood vessels, coatings for cells such as islets of Langerhans, and coatings, plugs, supports or substrates for contact with biological materials such as the body, and as drug delivery devices for biologically active molecules. A medical condition at a localized site is treated by applying a polymerization initiator and then applying a substantially water-soluble, degradable macromer of at least 200 mw and having at least two crosslinkable substituents, and polymerizing the macromer to form a crosslinked polymeric material at the site. The crosslinked polymeric material may adhere two surfaces together, or be a barrier that provides immunoisolation or prevents adhesion of the site to another surface such as post-surgical adhesion. A biologically active material may be present when the macromer is polymerized to provide for delivery of the biologically active material, or to provide the polymeric material with a desired property such as resistance to bacterial growth or a decrease in inflammatory response.

17 Claims, 7 Drawing Sheets

U.S. PATENT DOCUMENTS

| | | | | |
|---|---|---|---|---|
| 4,745,160 | A | 5/1988 | Churchill et al. | 525/415 |
| 4,774,178 | A | 9/1988 | Egerer et al. | 435/41 |
| 4,791,061 | A | 12/1988 | Sumino et al. | 435/178 |
| 4,804,691 | A | 2/1989 | English et al. | 523/118 |
| 4,806,355 | A | 2/1989 | Goosen et al. | 424/424 |
| 4,822,535 | A | 4/1989 | Ekman et al. | 264/4.3 |
| 4,826,945 | A | 5/1989 | Cohn et al. | 424/423 |
| 4,888,413 | A | 12/1989 | Domb | 424/78.17 |
| 4,889,722 | A | 12/1989 | Sheffield et al. | 424/450 |
| 4,913,903 | A | 4/1990 | Sudmann et al. | 424/426 |
| 4,916,193 | A | 4/1990 | Tang et al. | 525/413 |
| 4,925,677 | A | 5/1990 | Feijen | 424/484 |
| 4,931,279 | A | 6/1990 | Bawa et al. | 424/487 |
| 4,938,763 | A | 7/1990 | Dunn et al. | 604/891.1 |
| 4,942,035 | A | 7/1990 | Churchill et al. | 514/15 |
| 4,950,596 | A | 8/1990 | Cheng et al. | 435/94 |
| 4,957,744 | A | 9/1990 | della Valle et al. | 424/401 |
| 5,037,656 | A | 8/1991 | Pitt et al. | 424/443 |
| 5,153,002 | A | 10/1992 | McMullen | 424/473 |
| 5,160,745 | A | 11/1992 | DeLuca et al. | 424/499 |
| 5,183,690 | A | 2/1993 | Carr et al. | 424/499 |
| 5,185,408 | A | 2/1993 | Tang et al. | 525/415 |
| 5,219,564 | A | 6/1993 | Zalipsky et al. | 424/78.17 |
| 5,268,182 | A | 12/1993 | Brinker et al. | 424/499 |
| 5,271,961 | A | 12/1993 | Mathiowitz et al. | 424/499 |
| 5,278,201 | A | 1/1994 | Dunn et al. | 523/113 |
| 5,278,202 | A | 1/1994 | Dunn et al. | 523/113 |
| 5,286,495 | A | 2/1994 | Batich et al. | 424/499 |
| 5,288,500 | A | 2/1994 | Ibsen | 424/499 |
| 5,334,640 | A | 8/1994 | Desai et al. | 524/56 |
| 5,410,016 | A | 4/1995 | Hubbell et al. | 528/185 |
| 5,432,210 | A | 7/1995 | Bogan, Jr. | 523/201 |
| 5,529,914 | A | * 6/1996 | Hubbell et al. | 435/182 |
| 5,573,934 | A | * 11/1996 | Hubbell et al. | 435/177 |
| 5,834,274 | A | * 11/1998 | Hubbell et al. | 435/177 |
| 5,837,747 | A | * 11/1998 | Soon-Shiong et al. | 522/26 |
| 5,843,743 | A | * 12/1998 | Hubbell et al. | 435/177 |

OTHER PUBLICATIONS

Andrade, et al., "Protein Adsorption and Materials Biocompatability: A Tutorial Review and Suggested Hypothesis," *Advances in Polymer Science,* published by Springer–Verlag Berlin Heidelberg, pp. 1–63 (1986).

Buck, "Cell Surface Receptors for Extracellular Matrix Molecules," *Ann. Rev. Cell Bio.* 3:179–205 (1987).

Chesneau, et al., "Polymerization induito sous Irradiation Lager Visible," *J. Bio. Ang. Chemie.* 135:41–64 (1985).

Chiang, et al., "Preparation and Properties of UV–Autocurable BTDA–Based Polyester Multiacrylates. I. Effects of Acrylic Functionality and Polyl Molecular Weight," *J. App. Pol. Sci.* 41:2971–2985 (1990).

Cohn, et al., "Biodegradable PEO/PLA Block Copolymer," *J. Biomed. Materials Research* 22:993–1009 (1988).

Coleman, et al., "Blood–materials interactions: The Minimum Interfacial free energy and the optimum polar/apolar ratio hypothesis," *J. Biomed. Materials Res.* 16:381–398 (1982).

Crooks, et al., "Microencapsulation of Mammalian Cells in a HEMA–MMA Copolymer: Effects on Capsule Morphology and Permeability," *J. of Biomedical Materials Res.* 24:1241–1262 (1990).

Darquy, et al., "Immunoisolation of pancreatic a cells by microencapsulation—an in vitro study," *Diabetologia* 28:776–780 (1985).

Desai, et al., "The short–term blood biocompatability of poly(hydroxyethyl methacrylate–co–methyl methacrylate) in an in vitro flow system measured by the digital vieomicroscopy," *J. Biomaterial Sci. Polymer Ed.* 1(2):123–146 (1989).

Desai, et al., "Surface Modifications of Polymeric Biomaterials for Reduced Thrombogenicity," *Polymeric Materials Science and Engineering Proceedings of the ACS Division of Polymeric Materials Science and Engineering* 62:731–735 (1990).

Desai, et al., "Solution Technique to Incorporate Polyethylene Oxide and other Water–soluble Polymers into Surfaces of Polymeric Biomaterials," *Biomaterials* 12:144–153 (1991).

Desai, et al. "Surface Physical Interpenetrating Networks of Poly(ethylene terephthalate) and Poly(ethyleen oxide) with Biomedical Applications," *Macromolecules* 25:226–232 (1992).

Diamond, et al., "Synergistic effects of Interceed (Tc7) and heparin in reducing adhesion formation in the rabbit uterine horn model," *Fertility and Sterility* 55(2):389–394 (1991).

Domb, et al., "Poly(anhydrides). 3. Poly(anhydrides) Based on Aliphatic Aromatic Diacids," *J. Macromolecules* 22:3200–3204 (1989).

Doody, et al, "Recombinant tissue plasminogen activator reduces adhesion formation in a rabbit uterine horn model," *Fertility and Sterility* 51(3):509–512 (1989).

Dunn, et al., "Synergistic Effect of Intraperitoneally administered calciium channel blockade and recombinant tissue-plasminogen activator to preven adhesion formation in an animal model," *Am. J. Obstet. and Gynecol.* 164(5):1327–1330 (1991).

Dupuy, et al., "Microencapsulation of Isolated Pituitary Cells by Polyacrylamide Microlatex Coagulation on Agarose Beads," *Biomaterials* 12:493–495 (1991).

Eaton, "Dye Sensitized Photopolymerization," *Advances in Photochemistry,* 13:427–481 (John Wiley & Sons, Inc. 1986).

Epaillard, et al., "Plasma Induced Polymerization," *J. Applied Polymer Sci.* 38:887–898 (1989).

Fuértges, et al., "The Clinical Efficacy of Poly(Ethylene Glycol) Modified Proteins," *J. Controlled Release* 11:139–148 (1990).

Fukui, et al., "Application of Photo–Crosslinkable Resin to Immobilization of an Enzyme," *FEBS Letters* 66(2):179–182 (1976).

Fukui, et al., "Applications of Biocatalystic Immobilized by Prepolymer Methods," *Adv. of Biochemical Eng. and Biotech.* 201:1–33 (1984).

Fukui, et al., "Entrapment of Biocatalysts with Photo–Cross–Linkable Resin Prepolymers and Urethane Resin Prepolymers," *Methods in Enzymology* 135:230–253 (1987).

Fukui, et al., "Several novel methods for immobilization of enzymes microbial cells and organelles," *Biochimie* 62:381–386 (1980).

Fukuzai, et al., "A new biodegradable copolymer of glycolic acid and lactones with relatively low molecular weight prepared by direct copolycondensation in the absence of catallysts," *J. of Biomedical Materials Research* 25:315–328 (1991).

Gabbay, et al., "New Outlook on Pericardial Substitution After Open Heart Operations," *ann. Thorac. Surg.* 48:803–812 (1989).

Gharapatian, et al., "Encapsulation of Viable Cells Within Polyacrylate Membranes," *Biotechnology and Bioengineering* 28:1595–1600 (1986).

Gharapatian, et al., "Polyacrylate Microcapsules for Cell Encapsulation: Effects of Copolymer Structure on Membrane Properties," *Biotechnology and Bioengineering* 30:775–779 (1987).

Gibble, et al., "Fibrin glue: the perfect operative sealant?," *Transfusion* 30(8):741–747 (1990).

Gin, et al., "Agarose Encapsulation of Islets of Langerhans: Reduced Toxicity in vitro," *J. Microencapsulation* 4:239–242 (1987).

Golander, et al., "Preparation and Protein Adsorption Properties of Photopolymerized Hydrophilic Films Containing N–Vinylpyrrolidone (NVP), Acrylic Acid (AA) or Ethyleneoxide (EO) Units as Studiced by ESCA," *Colloids and Surfaces* 21:149–165 (1986).

Goldberg, et al., "An Evaluation of the Gore–Tex Surgical Membrane for the Prevention of Postoperative Peritoneal Adhesion," *Obstetrics and Gynecology* 70(6):846–848 (1987).

Gombotz, et al., "Immobilization of Poly(ethylene Oxide) on Poly(ethylene Terephthalate) Using a Plasma Polymerization Process," *J. of Applied Polymer Science* 37:91–107 (1989).

Goosen, et al., "Optimization of Microencapsulation Parameters: Semipermeable Microcapsules as a Bioartificial Pancreas," *Biotechnology and Bioengineering* vol. 27:146–150 (1985).

Graham, et al., "Hydrogels for controlled drug delivery," *Biomaterials* 5:27–36 (1994).

Harris, "Laboratory Synthesis of Polyethylene Glycol Derivatives," *Micromol. Chem. Phys.* C25(3):325–373 (1985).

Hattori, et al., "Fibroblast Cell Proliferation on Charged Hydroxyethyl Methacrylate Copolymers," *J. of Colloid and Interface Science* 104:72–78 (1985).

Heller, et al., "Controlled release of water–soluble macromolecules from bioerodible hydrogels," *Biomat.* 40:262–266 (1983).

Heller, et al., "Poly(ortho esters)," *Biodegradable Polymers as Drug Delivery System* (Chasin, et al., eds.), pp. 121–161 (1990).

Holland, et al., "Polymers for Biodegradable Medical Devices. 1. The Potential of Polyesters as Controlled Macromolecular Release Systems," *J. Controlled Release* 4:155–180 (1986).

Holtz, "Prevention and Management of Peritoneal Adhesions," *Fertility and Sterility* 42(4):497–507 (1984).

Horbett, "Mass Action Effects on Competitive Adsorpotion of Fibrinogen from Hemoglobin Solutions and from Plasma," *Rhromb. Haomostas.* (Stuttgart), 51(2):174–181 (1984).

Hu, et al., "Effect of soft segment in degradation kinetics in polyethylene glycol/poly(L–lactide) block copolymers," *Polymer Bulletin* 30:669–676 (1993).

Huffman, et al., "Effect of Carboxyl End Groups on Hydrolysis of Polyglycolic Acid," *J. Polymer Science, Polymer Chemistry Edition* 23:1939–1951 (1985).

Hunt, et al., "Synthesis and Evaluation of a Prototypal Artificial Red Cell," *Science* 6:1165–1168 (1985).

Hunter, et al., "Surface Modification of Polyurethane to Promote Long–Term Patency of Peritoneal Access Devises," *Trans. Am. Soc. Artif. Intern. Organs* 29:250–254 (1983).

Interceed (TC7) Adhesion Barrier Study Group, "Prevention of Postsurgical adhesions by Interceed (TC7), an absorbable adhesion barier: a prospective, randomized multicenter clinical study," *Fertility and Sterility* 51(6):933–938 (1989).

Itoh, et al., "Development of Novel Photocurable Medical–Use Resins; Molecular Design Considerations and Basic Properties," *Jap. J. Artif. Organs* 18(1):132–136 (1989).

Iwata, et al., "The Use of Photocrosslinkable Polyvinyl Alcohol in the Immunoisolation of Pancreatic Islets," *Transplantations Proceedings* 22(2):797–799 (1990).

Kanako, et al., CA 84:123221g, "Radiation–induced graft copolymerization to polyester, XVII. Grafting of polyethylene glycol dimethacrylates and diacrylates onto poly(ethylene terephthalate) fabric with electron beams," *Nippon Genshiryoky Kenkyusho Nempo* 5030:48–59 (1975).

Karu, "Yearly Review—Effects of Visable Radiation on Cultured Cells," *Photochemistry and Photobiology* 52(6):1089–1098 (1990).

Kenley, et al., "Poly(lactide–co–glycolide) Decomposition Kinetics in vivo and in vitro," *Macromolecules* 20:2398–2403 (1987).

King, et al., "Alginate–Polylysine Microcapsules of Controlled Membrane Molecular Weight Cutoff for Mammalian Cell Culture Engineering," *Biotechnology Progress* 3(4):231–240 (1987).

Kobayashi, et al., "Water–Curable and Biodegradable Prepolymers," *J. Biomed. Mat. Res.* 25:1481–1494 (1991).

Koshiba, et al., "Properties of Ultra–Violet Curable Polyurethane Acrylates," *J. Materials Sci.* 17:1447–1458 (1982).

Kricheldorf, et al., "ABA Triblock Copolymers of L–Lactide and Poly(ethylene glycol)," *Makromol. Chem.* 194:715–725 (1993).

Kulkarni, et al, "Polylactic Acid for Surgical Implants," *Arch. Surg.* 93:841–845 (1966).

Kulkarni, et al., "Biodegradable Poly(actic acid) Polymers," *J. Biomed. Mater. Res.* 5:169–181 (1971).

Kumakura, et al., "Immobilization of Microbial Cells in Membrane Form by Radiation–Induced Cast–Polymerization," *Die Angewandte Makromol. Chemis.* 115:75–86 (1986).

Lacy, et al., "Maintenance of Normoglycemia in Diabetic Mice by Subcutaneous Xenografts of Encapsulated Islets," *Science* 254:1782–1794 (1991).

Leach, et al., "Reduction of postoperative adhesions int he rat uterine horn model with polyxamer 407," *Am. J. Obstet. Gynecol.* 162(5):1317–1319 (1990).

Lee, et al., "Protein–resistant surfaces prepared by PEO–containing block copolymer surfactants," *J. Biomedial Materials Research* 23:351–368 (1989).

Lim, et al., "Microencapsulated islets as Bioartificial Endocrine Pancreas," *Science* 210:908–910 (1980).

Lin, et al., "Optically Clear Simultaneous Interpenetrating Polymer Networks Based on Poly(ethylene glycol) Diacrylate and Epoxy. Preparation and Characterization," *J. Polymer Sci.* 30:1941–1951 (1992).

Lipatoya, "Medical Polymer Adhesives," *Advances in Polym. Sci.* 79:85–92 (1986).

Maechling–Strasser, et al., "Peadsorption of polymers on glass and silica to reduce fibrinogen adsorption," *J. of Biomedical Materials Research* 23:1385–1393 (1989).

Mallabone, et al., "Microencapsulation of Human Diploid Fibroblasts in Cationic Polyacrylates," *Dept. of Chem. Eng. and Applied Chem. and Centre for Biomaterials* (1989).

Matsuda, et al., "Photoinduced Prevention of Tissue Adhesion," *ASAIO Trans.* 38:M154–M155 (1992).

Mayer, et al., "Effect of viscous macromolecules on peritoneal plasminogen activator activity: A potential mechanism for their ability to reduce postoperative adhesion formation," *Am. J. Obstet. Gynecol.* 159(4):957–963 (1988).

Menzies, et al., "The Role of Plasminogen Activator in Adhesion Prevention," *Surgery Gynecology and Obstetr.* 172:362–366 (1991).

Merrill, et al., "Platelet–Compatible Hydrophilic Segmented Polyurethanes From Polyethylene Glycols and Cyclohexane Diisoccyanate," *Trans. Am. Soc. Artif. Intern. Organs* 28:482–487 (1982).

Miller, et al., "Degradation Rates of Oral Resorbable Implants (Polylactates and Polyglycolates): Rate Modification with Changes in PLA/PGA Copolymer Ratios," *J. Biomed. Mater. Res.* 11:711–719 (1977).

Miyake, et al., "Solution Properties of Synthetic Polypeptides. XVIII: Helix–Coil Transition of Poly–m2–(2–Hydroxyethyl)L–Glutamine," *Biopolymers* 13:1173–1186 (1974).

Miyama, et al., "Graft Copolymerization of Methoxypoly (ethylene Glycohol) Methacrylate onto Polyacrylonitrile and Evaluation of Nonthrombogenicity of the Copolymer," *Journal of Applied Polymer Science* 35:115–125 (1988).

Mori, et al., "A New Antithrombogenic Material with Long Polyethylenoxide Chains," *Trans. Am. Soc. Artif. Intern. Organs* 28:459–463 (1982).

Nagaoka, et al., "Clinical application of antithrombogenic hydrogel with long poly(ethylene oxide) chains," *Biomaterials* 11:119–121 (1990).

Nojiri, et al., "In Vivo Protein Adsorption onto Polymers: A Transmission Electron Microscopic Study," *Trans. Am. Soc. Artif. Intern. Organs* 35:357–361 (1989).

Okada, et al., "Application of Entrapped Growing Yeast Cells to Peptide Secretion System," *Appl. Microbiol. Biotechnol.* 26:112–116 (1987).

Omata, et al., "Immobilization of Microbiol Cells and Enzymes with Hydrophobic Photo–Crosslinkable Resin Prepolymers," *European J. Appl. Microbiol.* 6:207–215 (1979).

Omata, et al., "Transformation of Steroids by Gel–Entrapped Nocardia rhodocrous Cells in Organic Solvent," *Eur. J. Appl. Microbiol. Biotechnol.* 8:143–155 (1979).

Pagidas, et al., "Effect of Ringer's Lactate. Interceed (TC7) and Gore–Tex Surgical Membrane on Postsurgical Adhesion Formation," *Fertility and Sterility* 57(1):199–201 (1992).

Park, et al., "Immobilization of Arthrobactor–Simplex Cells In Thermally Reversible Hydrogels Comparative Effects of Organic Solvent and Polymeric Surfactant on Steroid Conversion," *Biotechnology Letters* 11(1):17–22 (1989).

Peterson, "Polyethylene Glycol Diacrylates as Embedding Media for Electron Microscopy," Thirtieth Annual Meeting, Electron Microscopy Society of America and First Pacific Regional Conference on Electron Microscopy, 144–145 (1972).

Philips, et al., "Radiation curable water dilutable polyester acrylates," *European Polymrs Paint Colour J.* 183(4322):38–40 (1993).

Pitt, et al., "Aliphatic Polyesters. I. The Degradation of Poly(ε–caprolactone) in vivo," *J. Applied Polymer Science* 26:3779–3787 (1981).

Pitt, et al., "Aliphatic polyesters. II. The degradation of poly(DL–lactide), poly (caprolactone), and their copolymers in vivo," *Biomaterials* 2:215–220 (1981).

Priola, et al., "Investigation on the structure–property relationships for films obtained from UV curable coatings," *Progress in Organic Coatings* 22:301–314 (1993).

Priola, et al, "Properties of polymeric films obtained from u.v. cured poly(ethylene glycol) diacrylates," *Polymer.* 34(17):3653–3657 (1993).

Punnonen, et al., "Polyethylene glycol 4000 in the prevention of peritoneal adhesions," *Fertility and Sterility* 38(4):491–492 (1982).

Rätzsch, et al., "Strahlkenchische Antielektrostatik–Ausrustung," *Acta. Polymerica* 41(8):453–460 (1990).

Reach, et al., "The U–Shaped Bioartificial Pancreas with Rapid Glucose–Insulin Kinetics," *Diabetes* 33:752–761 (1984).

Rempp, et al., "Anionically Polymerized Star Macromolecules Having Divinyl Benzene Cores with Grafted Poly-(Ethylene oxide) Arms as Biomaterials," Abstract, *Polymer Reprints* 31(1):215 (1990).

Ronel, et al., "Macroporous Hydrogen Membranes for a Hybrid Artificial Pancreas. I. Synthesis and Chamber Fabrication," *J. of Biomedical Materials Res.* 17(5):855–864 (1983).

Sawhney, et al., "Rapidly degraded terpolymers of dl–lactide, glycolide, and a–caprolactone with increased hydrophilicity by copolymerization with polyethers," *J. Biomedical Materials Research* 24:1397–1411 (1990).

Sawhney, et al., "Poly(ethylene oxide)–graft–poly(L–lysine) copolymers to enhance the biocompatability of poly(L–l–ysine)–alginate microcapsule membranes," *Biomaterials* 13(12):863–870 (1992).

Sefton, et al., "Hydrophilic Polyacrylates for the Microencapsulation of Fibroblasts or Pancreatic Islets," *J. of Controlled Release* 6:177–187 (1987).

Shimizu, et al., "Studies on Composites of Collagen and a Synthetic Polymer," *Biomat. Med. Dev. Art. Org.* 6(4):375–391 (1978).

Skarda, et al., "Biodegradable Hydrogel for Controlled Release of Biologically Active Macromolecules," *J. Bioactive and Compatible Polymers* 8:24–37 (1993).

Sonomoto, et al., "Growth of *Curvularia lunate* spores into mycelial form within various gels, and steroid 11β–hydroxylation by the entrapped mycelia," *J. Ferment. Technol.* 59(6):465–469 (1981).

Speckhard, et al., "Properties of UV–Curable Polyuthane Acrylates: Effect of Reactive Diluent," *J. Appl. Poly. Sci.* 30(2):647–666 (1985).

Spilizewski, et al., "The Effect of Hydrocortisone Acetate Loaded Poly(DL–lactide) Films on the Inflammatory Resonse," *J. Controlled Release* 2:197–203 (1985).

Steinleitner, et al., "Poloxamer 407 as an Intraperitoneal Barrier Material for the Prevention of Postsurgical Adhesion Formation and Reformation in Rodent Models for Reproductive Surgery," *Obstetrics and Gynecology* 77(1):48–52 (1991).

Stevenson, et al., "Graft Copolymer Emulsions of Sodium Alginate with Hydroxyalkyl Methacrylates for Microencapsulation," *Biomaterials* 8:449–457 (1987).

Stevenson, et al., "Microencapsulation of Mammilian Cells in a Hydroxyethyl Methacrylate–Methyl Methacrylate Copolymer: Preliminary Development," *Biomat. Art. Cells* 16:747–769 (1988).

Sun, et al., "Encapsulated Versus Modified Endocrine Cells for Organ Replacement," *Trans. Am. Soc. Artif. Intern. Organs* 33:787–790 (1987).

Suzuki, et al., "Microencapsulation and Dissolution Properties of a Neuroleptic In a Biodegradable Polymer, Poly (d,l–lactide)," *J. Pharmaceutical Sciences* 74(1):20–24 (1985).

Tanaka, et al., "Immobilization of Yeast Microbodies by Inclusion with Photo–crosslinkable Resins," *Eur. J. Biochem.* 80:193–197 (1977).

Thomas, ed., "Lumen," *Taber's Cyclopedic Medical Dictionary*, 12th Edition, p. L–49 (F.A. Davis Company, Philadelphia).

Thompson, et al., "Fibrin Glue: A Review of its Preparation Efficacy, and Adverse Effects as a Topical Hemostat," *Drug Intelligence and Clinical Pharmacy* 22:946–952 (1988).

Uretzky, et al., "Long–term evaluation of a new selectively biodegradable vascular graft coated with polyethylene oxide–polylactic acid for right ventricular conduit," *J. Thorac Cardiovasc. Surg.* 133:769–780 (1990).

Urman, et al., "Effect of hyaluronic acid on postoperative intraperitoneal adhesion formation and reformation in the rat model," *Fertility and Sterility* 56(3):568–570 (1990).

Urman, et al., "Effect of Hyaluronic acid on postoperative intraperitoneal adhesion formation and reformation in the rat model," *Fertility and Sterility* 56(3):563–567 (1991).

Van Neerbos, "Parameters in UV Curable Materials Which Influence Cure Speed," *J. Oil Col. Chem. Assoc.* 61(1):241–250 (1978).

Van Wachem, et al., "Adhesion of cultured human endothelial cells onto methacrylate polymers with varying surface wettability and charge," *Biomaterials* 8:323–328 (1987).

Visscher, et al., "Biodegradation of and tissue reaction to 50:50 poly(DL–lactide–co–glycolide) microcapsules," *J. Biomedical Materials Research* 19:349–365 (1985).

Wen, et al., "Microcapsules through Polymer Complexation," *Dept. of Chemistry and Inst. for Aviation Research* (1990).

Wong, et al., "The Viability and Regeneration of Artificial Cell Microencapsulated Rat Hepatocyte Xenograft Transplants in Mice," *Biomat.* 16(4):731–739 (1988).

Woodward, et al., "The Intracellular degradation of poly(c–caprolactone)," *J. Biomedical. Materials Research* 19:437–444 (1985).

Wujek, et al., "A Carbohydrate Polymer that Effectively Prevents Epidural Fibrosis at Laminectomy Sites in the Rat," *Exp. Neurology* 114:237–245 (1991).

Zhu, et al., "Preparation and Properties of D,L–Lactide and Ethylene Oxide Copolymer: A Modifying Biodegradable Polymeric Material," *J. Polymer Sci., Part C: Polymer Letters* 24:331–337 (1986).

Zhu, et al., "Super Microcapsules" (SMC), I. Preparation and Characterization of Star Polyethylene Oxide (PEO)–Polylactide (PLA) Copolymers, *J. Polymer Sci.: Part A: Polymer Chemistry* 27:2151–2159 (1989).

Zhu, et al., "Preparation Characterization and Properties of Polylactide (PLA)–Poly(ethylene Glycol) (PEG) Copolymers: A Potential Drug Carrier," *J. Applied Sci.* 39:1–9 (1990).

* cited by examiner

TREATING MEDICAL CONDITIONS BY POLYMERIZING MACROMERS TO FORM POLYMERIC MATERIALS

BACKGROUND OF THE INVENTION

This is a continuation of application Ser. No. 08/467,693, filed Jun. 6, 1995, now U.S. Pat. No. 5,834,274, which is a divisional of prior application Ser. No. 08/024,657 filed on Mar. 1, 1993, now U.S. Pat. No. 5,573,934, which is a continuation-in-part of U.S. Ser. No. 07/958,870, filed Oct. 7, 1992, now U.S. Pat. No. 5,529,914, which is a continuation-in-part of U.S. Ser. No. 07/870,540, filed Apr. 20, 1992 now abandoned. This application is also a continuation-in-part of Ser. No. 08/475,175, filed Jun. 7, 1995, now U.S. Pat. No. 5,846,530, which is a divisional of U.S. Ser. No. 08/232,054, filed Apr. 28, 1994, now U.S. Pat. No. 5,837,747.

FIELD OF THE INVENTION

The present invention relates to methods for coating and/or encapsulating surfaces and three-dimensional objects with cross-linked networks of water-soluble polymers.

Microencapsulation technology holds promise in many areas of medicine. For example, some important applications are encapsulation of cells for the treatment of diabetes (Lim, F., sun, A. M. "Microencapsulated islets as bioartificial endocrine pancreas", (1980) *Science* 210, 908–910), encapsulation of hemoglobin for red blood cell substitutes, and controlled release of drugs. However, using the prior art methods, the materials to be encapsulated are often exposed to processing conditions, including heat, organic solvents and non-physiological pHs, which can kill or functionally impair cells or denature proteins, resulting in loss of biological activity. Further, even if cells survive the processing conditions, the stringent requirements of biocompatibility, chemical stability, immunoprotection and resistance to cellular overgrowth, of the encapsulating materials restrict the applicability of prior art methods.

For example, the encapsulating method based on ionic crosslinking of alginate (a polyanion) with polylysine or polyornithine (polycation) (Goosen, et al., (1985) *Biotechnology and Bioengineering*, 27:146) offers relatively mild encapsulating conditions, but the long-term mechanical and chemical stability of such ionically crosslinked polymers remains doubtful. Moreover, these polymers when implanted in vivo are susceptible to cellular overgrowth (McMahon, et al., (1990) *J. Nat. Cancer Inst.*, 82(22), 1761–1765) which over time restricts the permeability of the microcapsule to nutrients, metabolites and transport proteins from the surroundings. This has lead to starvation and death of encapsulated islets of Langerhorns (O'Shea, G. M. et al. (1986) *Diabetes*, 35:943–946).

Thus, there remains a need for a relatively mild cell encapsulation method which offers control over properties of the encapsulating polymer and yields membranes in the presence of cells which are permselective, chemically stable, and very highly biocompatible. A similar need exists for the encapsulation of biological materials other than cells and tissues, as well as materials contacting biological materials.

Materials are considered biocompatible if the material elicits either a reduced specific humoral or cellular immune response or does not elicit a nonspecific foreign body response that prevents the material from performing the intended function, and if the material is not toxic upon ingestion or implantation. The material must also not elicit a specific reaction such as thrombosis if in contact with the blood.

Gels made of polymers which swell in water to form a hydrogel, such as poly(hydroxyethyl methacrylate) (poly (HEMA)), water-insoluble polyacrylates, and agarose, have been shown to be useful for encapsulating islets and other animal tissue (Iwata, et al., (1989) *Diabetes*, 38:224–225; Lamberti, et al., (1984) *Appl. Biochem. Biotech.*, 10, 101–105 (1984). However, these gels have undesirable mechanical properties. Agarose forms a weak gel, and the polyacrylates must be precipitated from organic solvents, which are potentially cytotoxic. Dupuy, et al. (1988) have reported the microencapsulation of islets by polymerization of acrylamide to form polyacrylamide gels. However, the polymerization process requires the presence of toxic monomers such as acrylamide and cross-linkers, and, if allowed to proceed rapidly to completion, generates local heat.

Microcapsules formed by the coacervation of alginate and poly(L-lysine) have been shown to be immunoprotective, for example, as described by O'Shea, et al., 1986. However, a severe fibrous overgrowth of these microcapsules was observed following implantation (McMahon, et al. 1990; O'Shea, et al., 1986). The use of poly(ethylene oxide) (PEO) to increase biocompatibility is well documented in literature. The biocompatibility of alginpoly(L-lysine) microcapsules has been reported to be significantly enhanced by incorporating a graft copolymer of PLL and PEO on the microcapsule surface (Sawhney, et al., "Poly(ethylene oxide)-Graft-Poly(L-Lysine) Copolymers to Enhance the Biocompatibility of Poly(L-Lysine)-Alginate Microcapsule Membranes," (1991) *Biomaterials*, 13, 863–870).

The PEO chain is highly water soluble and highly flexible. PEO chains have an extremely high motility in water and are essentially non-ionic in structure. Immobilization of PEO on a surface has been largely carried out by the synthesis of graft copolymers having PEO side chains (Sawhney, et al.; Miyama, et al., 1988; Nagoaka, et al.). This process involves the custom synthesis of monomers and polymers for each application. The use of graft copolymers, however, still does not guarantee that the surface "seen" by a macromolecule consists entirely of PEO.

Electron beam cross-linking has been used to synthesize PEO hydrogels, which have been reported to be non-thrombogenic by Sun, et al., (1987) *Polymer Prepr.*, 28:292–294; Dennison, K. A., (1986) Ph.D. Thesis. Massachusetts Institute of Technology. However, use of an electron beam precludes including with the polymer any living tissue since the radiation is cytotoxic. Also, the networks produced by this method are difficult to characterize due to the non-specific cross-linking induced by the electron beam.

Photopolymerization of PEG diacrylates in the presence of short wavelength ultraviolet light initiation has been used to entrap yeast cells for fermentation and chemical conversion (Kimura, et al. (1981), "Some properties of immobilized glycolysis system of yeast in fermentative phosphorylation of nucleotides," *Eur. J. Appl. Microbio. Biotechnol.*, 11:78–80; Omata et al., (1981), "Steroselectic hydrolysis of dl-methyl succinate by gel-entrapped Rhodotorula minuta uzr. texensis cells in organic solvent," *Eur. J. Appl. Microbial Biotechnol*, 11:199–204; Okada, T., et al., "Application of Entrapped Growing Yeast Cells to Peptide Secretion System," Appl. Microbiol. Biotechnol., Vol. 26, pp. 112–116 (1987). Other methods for encapsulation of cells within materials photopolymerizable with short wavelength ultraviolet radiation have been used with microbial cells (Kimura, et al., 1981; Omata, et al., 981; Okada, et al., 1987; Tanaka, et al., 1977; Omata, et al., 1979a; Omata, et al., 1979b; Chun, et al., 1981; Fukui, et al., 1976; Fukui, et al., 1984). However, yeast cells and some microbial cells are much hardier and resistant to adverse environments, elevated temperatures, and short wavelength ultraviolet radiation than mammalian cells and human tissues.

There are several problems with these methods, including the use of methods and/or materials which are thrombogenic or unstable in vivo, or require polymerization conditions which tend to destroy living mammalian tissue or biologically active molecules, for example, short wavelength ultraviolet radiation. In order to encapsulate living tissue for implantation in a human or other mammalian subject, the polymerization conditions must not destroy the living tissue, and the resulting polymer-coated cells must be biocompatible.

There is also a need to encapsulate materials within a very thin layer of material that is permeable to nutrients and gases, yet strong and non-immunogenic. For example, for transplantation of islets of Langerhans, the islets, which have a diameter of 100 to 200 microns, have in the past been encapsulated within microspheres that have a diameter of 400 to 1000 microns. This large diameter can result in slowed diffusion of nutritional molecules and large transplantation volumes.

In summary, there is a need for materials, and methods of use thereof, which can be used to encapsulate cells and tissues or biologically active molecules which are biocompatible, do not elicit specific or non-specific immune responses, and which can be polymerized in contact with living cells or tissue without injuring or killing the cells, within a very short time frame, and in a very thin layer. An important aspect of the use of these materials in vivo is that they must be polymerizable within the time of a short surgical procedure or before the material to be encapsulated disperses, is damaged or dies.

It is therefore an object of the present invention to provide a polymeric material that can be polymerized in contact with living cells and tissues, and in a very short time period.

It is a further object of the present invention to provide a polymeric material which is biocompatible and resistant to degradation for a specific time period.

It is a still further object of the present invention to provide a polymeric material which is permeable to nutrients and gases yet can protect cells and tissues from in vivo attack by other cells.

SUMMARY OF THE INVENTION

Disclosed herein is a method for polymerization of macromers using visible or long wavelength ultraviolet light (lw uv light, 320 nm or greater) to encapsulate or coat either directly or indirectly living tissue with polymeric coatings which conform to the surfaces of cells, tissues or carriers thereof under rapid and mild polymerization conditions; Polymers are formed from non-toxic pre-polymers, referred to herein as macromers, that are water-soluble or substantially water soluble and too large to diffuse into the cells to be coated. Examples of macromers include highly biocompatible PEG hydrogels, which can be rapidly formed in the presence or absence of oxygen, without use of toxic polymerization initiators, at room or physiological temperatures, and at physiological pH. Polymerization may be initiated using non-toxic dyes such as methylene blue or eosin Y, which are photopolymerizable with visible or lw uv light. Other dyes that diffuse into the cells but are nontoxic, such as ethyl eosin, may also be used. The process is non-cytotoxic because little light is absorbed by cells in the absence of the proper chromophore. Cells are largely transparent to this light, as opposed to short wavelength UV radiation, which is strongly absorbed by cellular proteins and nucleic acids and can be cytotoxic. Low levels of irradiation (5–500 mW) are usually enough to induce polymerization in a time period of between milliseconds to a few seconds for most macromers. A second reason for the lack of cytotoxicity is that the polymerizable species does not diffuse into cells.

The resulting polymers can act as semipermeable membranes, as adhesives as tissue supports, as plugs, as barriers to prevent the interaction of one cell tissue with another cell or tissue, and as carriers for bioactive species. A wide variety of surfaces, with different geometries, can be coated with a three dimensionally cross-linked network of these polymeric materials. The polymers can be formed into a matrix for delivery of biologically active materials, including proteins, polysaccharides, organic compounds with drug activity, and nucleic acids.

In one preferred embodiment, the polymer is used to form a layer on the inside of the lumen of a blood vessel, either for structural support, prevention of thrombosis and inflammatory reactions at the lumen surface, and/or delivery of therapeutic agents to the blood vessel. In another preferred embodiment, the polymer is used to create a semipermeable barrier around cells such as islets of Langerhans to protect the cell by preventing the passage of immunoglobulins molecules or cells, while allowing free transfer of nutrients, gases and small cell products. Such treated islets may be useful in treating diseases which result from deficiencies in metabolic processing, or diseases like diabetes which arise from insufficient concentrations of bioregulator molecules.

DETAILED DESCRIPTION OF THE INVENTION

Figure 1:
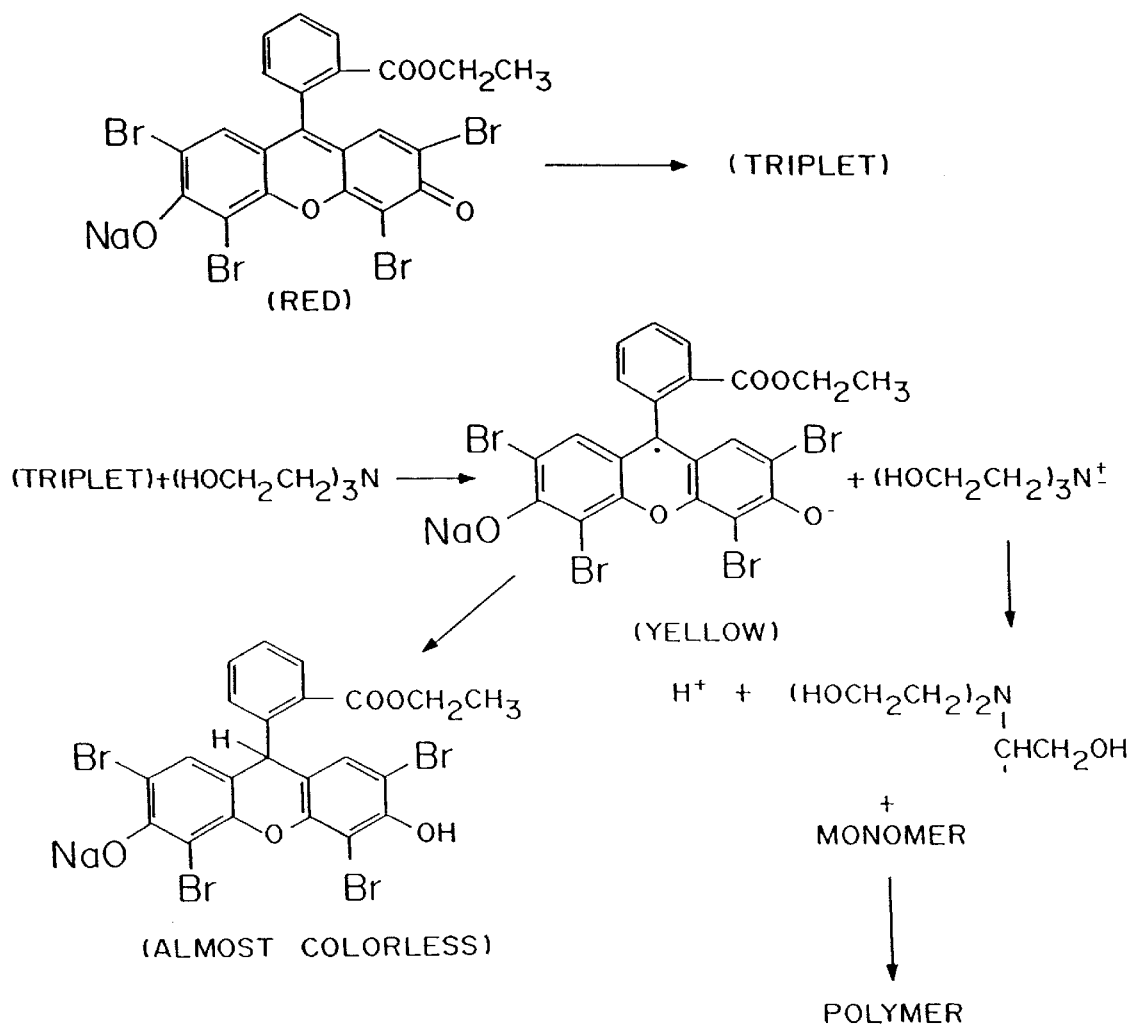
FIG. 1 is a reaction scheme for ethyl eosin initiated polymerization.
Figure 2:
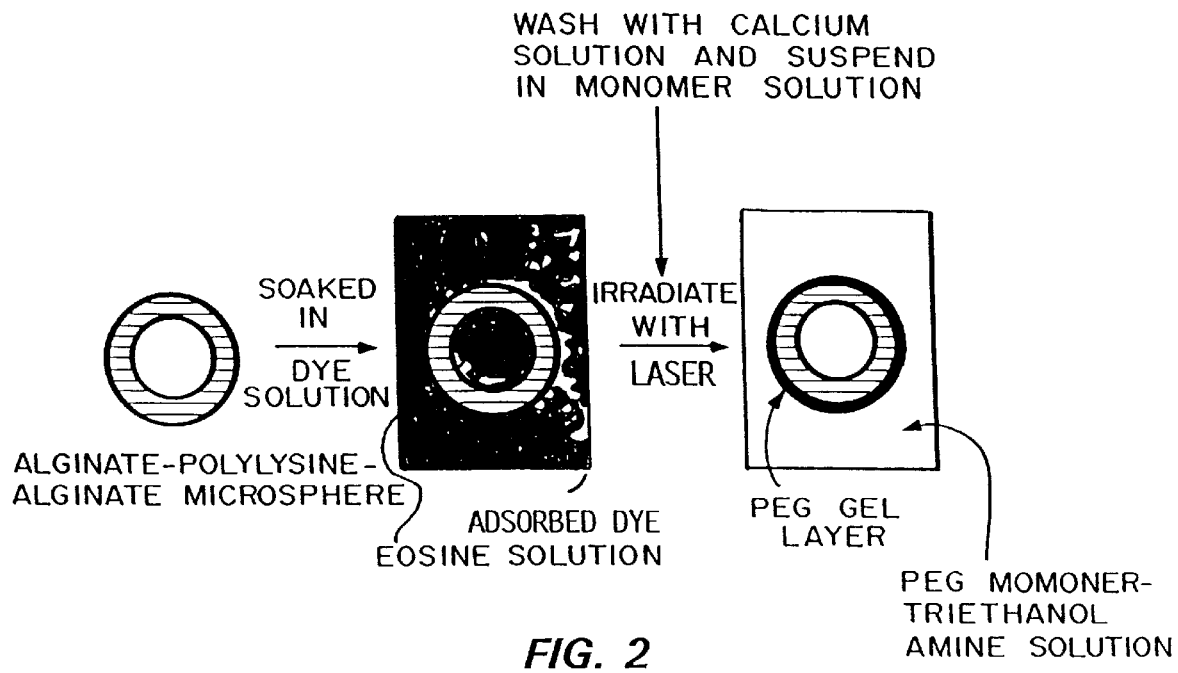
FIG. 2 is a schematic of dye-initiated polymerization of a PEG layer around crosslinked alginate microspheres.

As described herein, biocompatible polymeric materials are formed for use in juxtaposition with biologically active materials or cells and tissue, by free radical polymerization of biocompatible water soluble macromers including at least two polymerizable substituents. These polymeric coating materials can be either homopolymers, copolymers or block copolymers. As used herein, a polymer is a unit formed having a degree of polymerization greater than 10, and an oligomer has a degree of polymerization of between 2 and 10, degree of polymerization meaning the number of repeat units in the structure, e.g., d.p.=3 refers to a trimer. Polymerization of a component that has at least two polymerizable substituents is equal to gelation; the polymerization proceeds to form a three-dimensional, cross-linked gel.

Pre-polymers (Macromers) useful for Making Gels.

The general criteria for pre-polymers (referred to herein as macromers) that can be polymerized in contact with biological materials or cells are that: they are water-soluble or substantially water soluble, they can be further polymerized or crosslinked by free radical polymerization, they are non-toxic and they are too large to diffuse into cells, i.e., greater than 200 molecular weight. Substantially water soluble is defined herein as being soluble in a mixture of water and organic solvent(s), where water makes up the majority of the mixture of solvents.

As used herein, the macromers must be photopolymerizable with light alone or in the presence of an initiator and/or catalyst, such as a free radical photoinitiator, wherein the light is in the visible or long wavelength ultraviolet range, that is, greater than or equal to 320 nm. Other reactive conditions may be suitable to initiate free radical polymerization if they do not adversely affect the viability of the living tissue to be encapsulated. The macromers must also not generate products or heat levels that are toxic to living tissue during polymerization. The catalyst or free radical initiator must also not be toxic under the conditions of use.

A wide variety of substantially water soluble polymers exist, some of which are illustrated schematically below. (_) represents a substantially water soluble region of the polymer, and (=) represents a free radical polymerizable species. Examples include:

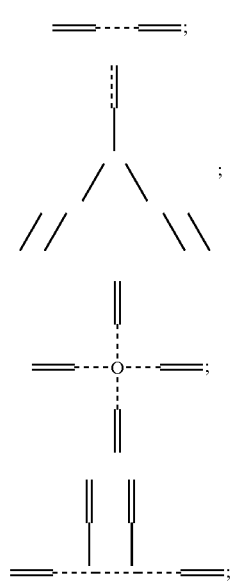

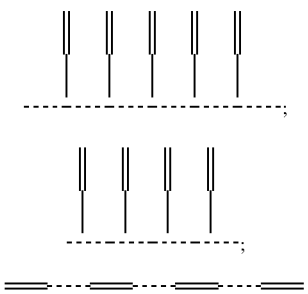

Examples of A include PEG diacrylate, from a PEG diol; of B include PEG triacrylate, formed from a PEG triol; of C include PEG-cyclodextrin tetraacrylate, formed by grafting PEG to a cyclodextrin central ring, and further acrylating; of D include PEG tetraacrylate, formed by grafting two PEG diols to a bis epoxide and further acrylating; of E include hyaluronic acid methacrylate, formed by acrylating many sites on a hyaluronic acid chain; of F include PEG-hyaluronic acid-multiacrylate, formed by grafting PEG to hyaluronic acid and further acrylating; of G include PEG-unsaturated diacid ester formed by esterifying a PEG diol with an unsaturated diacid.

Polysaccharides include, for example, alginate, hyaluronic acid, chondroitin sulfate, dextran, dextran sulfate, heparin, heparin sulfate, heparan sulfate, chitosan, gellan gum, xanthan gum, guar gum, and K-carrageenan. Proteins, for example, include gelatin, collagen, elastin and albumin, whether produced from natural or recombinant sources.

Photopolymerizable substituens preferably include acrylates, diacrylates, oligoacrylates, dimethacrylates, or oligomethoacrylates, and other biologically acceptable photopolymerizable groups.

Synthetic Polymeric Macromers.

The water-soluble macromer may be derived from water-soluble polymers including, but not limited to, poly(ethylene oxide) (PEO), poly(ethylene glycol) (PEG), poly(vinyl alcohol) (PVA) poly(vinylpyrrolidone) (PVP), poly(ethyloxazoline) (PEOX) polyaminoacids, pseudopolyamino acids, and polyethyloxazoline, as well as copolymers of these with each other or other water soluble polymers or water insoluble polymers, provided that the conjugate is water soluble. An example of a water soluble conjugate is a block copolymer of polyethylene glycol and polypropylene oxide, commercially available as a Pluronic™ surfactant.

Polysaccharide Macromers

Polysaccharides such as alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives, and carrageenan, which are linked by reaction with hydroxyls or amines on the polysaccharides can also be used to form the macromer solution.

Protein Macromers

Proteins such as gelatin, collagen, elastin, zein, and albumin, whether produced from natural or recombinant sources, which are made free-radical polymerization by the addition of carbon-carbon double or triple bond-containing moieties, including acrylate, diacrylate, methacrylate, ethacrylate, 2-phenyl acrylate, 2-chloro acrylate, 2-bromo acrylate, itaconate, oliogoacrylate, dimethacrylate, oligomethacrylate, acrylamide, methacrylamide, styrene groups, and other biologically acceptable photopolymerizable groups, can also be used to form the macromer solution.

Dye-sensitized Polymerization

Dye-sensitized polymerization is well known in the chemical literature. For example, light from an argon ion laser (514 nm), in the presence of an xanthin dye and an electron donor, such as triethanolamine, to catalyze initiation, serves to induce a free radical polymerization of the acrylic groups in a reaction mixture (Neckers, et al., (1989) *Polym. Materials Sci. Eng.*, 60:15; Fouassier, et al., (1991) *Makromol. Chem.*, 192:245–260). After absorbing the laser light, the dye is excited to a triplet state. The triplet state reacts with a tertiary amine such as the triethanolamine, producing a free radical which initiates the polymerization reaction. Polymerization is extremely rapid and is dependent on the functionality of the macromer and its concentration, light intensity, and the concentration of dye and amine.

Photoinitiating Dyes

Any dye can be used which absorbs light having a frequency between 320 nm and 900 nm, can form free radicals, is at least partally water soluble, and is non-toxic to the biological material at the concentration used for polymerization. There are a large number of ohotosensitive dyes that can be used to optically initiate polymerization, such as ethyl eosin, eosin Y, fluorescein, 2,2-dimethoxy-2-phenyl acetophenone, 2-methoxy,2-phenylacetophenone, camphorquinone, rose bengal, methylene blue, erythrosin, phloxime, thionine, riboflavin, methylene green, acridine orange, xanthine dye, and thioxanthine dyes.

The preferred initiator dye is ethyle eosin due to its spectral properties in aqueous solution (absorption max=528 nm, extinction coefficient=$1.1\times10^5$ $M^{-1}cm^{-1}$, fluorescence max=547 nm, quantum yield=0.59). A reaction scheme using ethyl eosin is shown in FIG. 1 as an example. The dye bleaches after illumination and reaction with amine into a colorless product, allowing further beam penetration into the reaction system.

Cocatalyst.

The cacatalysts useful with the photoinitiating dyes are nitrogen based compounds capable of stimulating the free radical reaction. Primary, secondary, tertiary or quaternary amines are suitable cocatalysts, as are any nitrogen atom containing electron-rich molecules. Cocatalysts include, but are not limited to, triethanolamine, triethylamine, ethanolamine, N-methyl diethanolamine, N,N-dimethyl benzylamine, dibenzyl amine, N-benzyl ethanolamine, N-isopropyl benzylamine, tetramethyl ethylenediamine, potassium persulfate, tetramethyl ethylenediamine, lysine, ornithine, histidine and arginine.

Examples of the dye/photoinitiator system includes ethyl eosin with an amine, eosin Y with an amine, 2,2-dimethoxy-2-phenoxyacetophenone, 2-methoxy-2-phenoxyacetophenone, camphorquinone with an amine, and rose bengal with an amine.

In some cases, the dye may absorb light and initiate polymerization, without any additional initiator such as the amine. In these cases, only the dye and the macromer need be present to initiate polymerization upon exposure to light. The generation of free radicals is terminated when the laser light is removed. Some photoinitiators, such as 2,2-dimethoxy-2-phenylacetophenone, do not require any auxiliary amine to induce photopolymerization; in these cases, only the presence of dye, macromer, and appropriate wavelength light is required.

Means for Polymerization.

Photopolymerization.

Preferred light sources include various lamps and lasers such as those described in the following examples, which have a wavelength of about 320–800 nm, most preferably about 365 nm or 514 nm.

This light can be provided by any appropriate source able to generate the desired radiation, such as a mercury lamp, longwave UV lamp, He-Ne laser, or an argon ion laser, or through the use of fiber optics.

Other Means for Polymerization.

Means other than light can be used for polymerization. Examples include initiation by thermal initiators, which form free radicals at moderate temperatures, such as benzoyl peroxide, with or without triethanolamine, potassium persulfate, with or without tetramethylethylenediamine, and ammonium persulfate with sodium bisulfite.

Incorporation of Biologically Active Materials.

The water soluble macromers can be polymerized around biologically active molecules to form a delivery system for the molecules or polymerized around cells, tissues, sub-cellular organelles or other sub-cellular components to encapsulate the, biological material. The water soluble macromers can also be polymerized to incorporate biologically active molecules to impart additional properties to the polymer, such as resistance to bacterial growth or decrease in inflammatory response, as well as to encapsulate tissues. A wide variety of biologically active material can be encapsulated or in corporated, including proteins, peptides, polysaccharides, organic or inorganic drugs, nucleic acids, sugars, cells, and tissues.

Examples of cells which can be encapsulated include primary cultures as well as established cell lines, including transformed cells. These include but are not limited to pancreatic islet cells, human foreskin fibroblasts, Chinese hamster ovary cells, beta cell insulomas, lymphoblastic leukemia cells, mouse 3T3 fibroblasts, dopamine secreting ventral mesencephalon cells, neuroblastoid cells, adrenal medulla cells, and T-cells. As can be seen from this partial list, cells of all types, including dermal, neural, blood, organ, muscle, glandular, reproductive, and immune system cells, as well as species of origin, can be encapsulated successfully by this method. Examples of proteins which can be encapsulated include hemoglobin, enzymes such as adenosine deaminase, enzyme systems, blood clotting factors, inhibitors or clot dissolving agents such as streptokinase and tissue plasminogen activator, antigens for immunization, and hormones, polysaccharides such as heparin, oligonucleotides such as antisense, bacteria and other microbial organisms, including viruses, vitamins, cofactors, and retroviruses for gene therapy can be encapsulated by these techniques.

The biological material can be first enclosed in a structure such as a polysaccharide gel. (Lim, U.S. Pat. No. 4,352,883; Lim, U.S. Pat. No. 4,391,909; Lim, U.S. Pat. No. 4,409,331; Tsang, et al., U.S. Pat. No. 4,663,286; Goosen et al., U.S. Pat. No. 4,673,556; Goosen et al., U.S. Pat. No. 4,689,293; Goosen et al., U.S. Pat. No. 4,806,355; Rha et al., U.S. Pat. No. 4,744,933; Rha et al., U.S. Pat. No. 4,749,620, incorporated herein by reference.) Such gels can provide additional structural protection to the material, as well as a secondary level of perm-selectivity.

Polymerization.

The macromers are preferably mixed with initiator, applied to the material or site where they are to be polymerized, and exposed to initiating agent, such as light or heat.

In a preferred method, a photo-initiating system is added to an aqueous solution of a photopolymerizable macromer to from an aqueous mixture; the biologically active material is added; and the aqueous solution irradiated with light. The macromer is preferably formed of a water soluble polymer with photopolymerizable substituents. Light absorption by the dye/initiator system results in the formation of free radicals which initiate polymerization.

In a second preferred method, macromer is coated on the surface of a three-dimensional object which may be of biological origin or a synthetic substrate for implantation in an animal. Water-soluble macromer is mixed with a photoinitiating system to form an aqueous mixture; the mixture is applied to a surface to be coated to form a coated surface; and the coated surface is irradiated with light to initiate macromer polymerization.

In a variation of this embodiment, the synthetic substrate can be a hydrophilic microsphere, microcapsule or bead. The hydrophilic microspheres are mixed with a water soluble macromer solution in combination with a photoinitiator system to form an aqueous mixture; the microspheres are suspended with agitation with macromer in oil to form an oil suspension, and the microspheres are irradiated with light.

In another particularly preferred embodiment, a photosensitive dye is absorbed to a tissue surface which is to be treated, the non-absorbed dye is diluted out or rinsed off the tissue, the macromer solution is applied to the dye-coupled surface, and polymerization initiated, to result in interfacial polymerization.

Polymerization can be effected by at least five different methods utilizing bulk polymerization or interfacial polymerization. These embodiments are further described below with respect to specific applications of the materials and processes for polymerization thereof.

Bulk Polymerization.

In bulk polymerization the material to be coated is placed in contact with a solution of macromer, photoinitiator and optionally cocatalyst, and then polymerization induced, for example, by exposure to radiation. Three examples of bulk polymerization follow:

Bulk Suspension Polymerization Method for Encapsulation of Material.

Biological material to be encapsulated is mixed with an aqueous macromer solution, including macromer, cocatalyst and optionally an accelerator, and initiator. Small globular geometric structures such as spheres, ovoids, or oblongs are formed, preferably either by coextrusion of the aqueous solution with air or with a non-miscible substance such as oil, preferably mineral oil, or by agitation of the aqueous phase in contact with a non-miscible phase such as an oil phase to form small droplets. The macromer in the globules is then polymerized by exposure to radiation. Because the macromer and initiator are confined to the globules, the structure resulting from polymerization is a capsule in which the biological material is enclosed. This is a "suspension polymerization" whereby the entire aqueous portion of the globule polymerizes to form a thick membrane around the cellular material.

Microcapsule Suspension Polymerization Method.

In a variation of the bulk suspension method, microencapsulated material is used as a core about which the macromer is polymerized in a suspension polymerization reaction. The biological material is first encapsulated within a microsphere, microcapsule, or microparticle (referred to herein collectively as microcapsules), for example, in alginate microcapsules. The microcapsules are then mixed with the macromer solution and initiator, and the macromer solution polymerized.

This method is particularly suitable for use with PEG macromers, taking advantage of the extreme hydrophilicity of PEG macromers, and is especially well adapted for use with hydrogel microcapsules such as alginate-poly(L-lysine). The microsphere is swollen in water. When a macromer solution containing catalyst and/or initiator or accelerator is forced to phase separate in a hydrophobic medium, such as mineral oil, the PEG macromer solution prefers to stay on the hydrophilic surface of the alginate microcapsule. When this suspension is irradiated, the PEG macromer undergoes polymerization and gelation, forming a thin layer of polymeric, water insoluble gel around the microsphere.

This technique preferably involves coextrusion of the microcapsule in a solution of macromer and initiator, the solution being in contact with air or a liquid which is non-miscible with water, to form droplets which fall into a solution such as mineral oil in which the droplets are not miscible. The non-miscible liquid is chosen for its ability to maintain droplet formation. Additionally, if the membrane-encapsulated material is to be injected or implanted in an animal, any residue should be non-toxic and non-immunogenic. Mineral oil is a preferred non-miscible liquid. Once the droplets have contacted the non-miscible liquid, they are polymerized.

This coextrusion technique results in a crosslinked polymer coat of greater than 50 microns thickness. Alternatively, the microcapsules may be suspended in a solution of macromer and initiator which is agitated in contact with a non-miscible phase such as an oil phase. The resulting emulsion is polymerized to form a polymer coat, also of greater than 50 microns thickness, around the microcapsules.

Bulk Polymerization Method for Tissue Adhesion.

The polymeric material can also be used to adhere tissue. A water soluble polymerizable macromer in combination with a photoinitiator is applied to a tissue surface to which tissue adhesion is desired; the tissue surface is contacted with the tissue with which adhesion is desired, forming a tissue junction; and the tissue junction is irradiated with light until the macromers are polymerized. In the preferred embodiment, this is accomplished in seconds up to minutes, most preferably seconds.

In the preferred embodiment, the macromer mixture is an aqueous solution, such as that of PEG 400 diacrylate or PEG 18.5 K tetraacrylate. When this solution contacts tissue which has a moist layer of mucous or fluid covering it, it intermixes with the moisture on the tissue. The mucous layer on tissue includes water soluble polysaccharides which intimately contact cellular surfaces. These, in turn, are rich in glycoproteins and proteoglycans. Thus, physical intermixing and forces of surface interlocking due to penetration into crevices, are some of the forces responsible for the adhesion of the PEG gel to a tissue surface subsequent to crosslinking.

Specific applications for such adhesives may include blood vessel anastomosis, soft tissue reconnection, drainable burn dressings, and retinal reattachment.

Bulk Polymerization to form Tissue Barriers

If the PEG gel is polymerized away from tissue, it then presents a very non-adhesive surface to cells and tissue in general, due to the highly hydrophilic nature of the material.

This feature can be exploited to form barriers upon tissues to prevent attachment of cells to the coated tissue. Examples of this application include the formation of barriers upon islets of Langerhans or upon the lumen of blood vessels to prevent thrombosis or vasospasm or vessel collapse; whether by bulk polymerization (with the polymerization initiator mixed in with the macromer) or by interfacial polymerization (with the initiator absorbed to the surface).

Interfacial Polymerization.

For interfacial polymerization, the free radical initiator is adsorbed to the surface of the material to be coated, non-adsorbed initiator is diluted out or rinsed off, using a rinsing solution or by application of the macromer solution, and the macromer solution, optionally containing a cocatalyst, is applied to the material, which is then polymerized. Two examples of interfacial polymerization follow:

Microcapsule Interfacial Polymerization Method.

Biological material can be encapsulated as described above with reference to suspension polymerization, but utilizing interfacial polymerization to form the membrane on the surface of the biological material or microcapsule. This involves coating the biological material or microcapsule with photoinitiator, suspending the biological material or microcapsules in the macromer solution, and immediately polymerizing, for example, by irradiating. A thin polymer coat, of less than 50 microns thickness, is formed around the biological materials or the microcapsules, because the photoinitiator is present only at the microcapsule surface and is given insufficient time to diffuse far into the macromer solution.

In most cases, initiator, such as a dye, will penetrate into the interior of the biological material or the microcapsule, as well as adsorbing to the surface. When macromer solution, optionally containing a cocatalyst such as triethanolamine, is applied to the surface and exposed to an initatiating agent such as laser light, all the essential components of the reaction are present only at and just inside the interface of the biological material or microcapsule and macromer solution. Hence, polymerization and gelation (if multifunctional macromer is used), which typically occurs within about 100 msec, initially takes place only at the interface, just beneath it, and just beyond it. If left for longer periods of time, initiator starts diffusing from the inner core of the microsphere into the solution; similarly, macromers start diffusing inside the core and a thicker layer of polymer is formed.

Direct Interfacial Polymerization Method.

Interfacial polymerization to form a membrane directly on the surface of tissues. Tissue is directly coated with initiator, excess initiator is removed, macromer solution is applied to the tissue and polymerized.

Control of Polymer Permeability.

The permeability of the coating is determined in part by the molecular weight and crosslinking of the polymer. For example, in the case of short PEG chains between crosslinks, the "pore" produced in the network will have relatively rigid boundaries and will be relatively small so that a macromolecule attempting to diffuse through this gel will be predominantly restricted by a sieving effect. If the chain length between crosslinks-is long, the chain can fold and move around with a high motility so that diffusing macromolecules will encounter a free volume exclusion effect as well as a sieving effect.

Due to these two contrasting effects a straightforward relation between molecular weight cutoff for diffusion and the molecular weight of the starting oligomer is not completely definable. Yet, a desired release profile for a particular protein or a drug such as a peptide can be accomplished by adjusting the crosslink density and length of PEG segments. Correspondingly, a desired protein permeability profile can be designed to permit the diffusion of nutrients, oxygen, carbon dioxide, waste products, hormones, growth factors, transport proteins, and secreted cellularly synthesized products such as proteins, while restricting the diffusion of immune modulators such as antibodies and complement proteins, as well as the ingress of cells, inside the gel, to protect transplanted cells or tissue. The three dimensional crosslinked covalently bonded polymeric network is chemically stable for long-term in vivo applications.

For purposes of encapsulating cells and tissue in a manner which prevents the passage of antibodies across the membrane but allows passage of nutrients essential for cellular metabolism, the preferred starting macromer size is in the range of between 10,000 D and 18,500 D, with the most preferred being around 18,500 D. Smaller macromers result in polymer membranes of a higher density with smaller pores.

Thickness and Conformation of Polvmer Layer.

Membrane thickness affects a variety of parameters, including perm-selectivity, rigidity, and size of the membrane. Thickness can be varied by selection of the reaction components and/or the reaction conditions. For example, the macromer concentration can be varied from a few percent to 100%, depending upon the macromer. Similarly, more intense illuminations and longer illuminations will yield thicker films than less intense or shorter illuminations will. Accelerators may also be added in varying concentration to control thickness. For example, N-vinylpyrrolidinone may be added as an accelerator, with higher concentrations yielding thicker layers than lower concentrations, all other conditions being equal. As an example, N-vinylpyrrolidinone concentrations can range from 0 to 0.5%.

In the interfacial polymerization method, the duration of the polymerization can be varied to adjust the thickness of the polymer membrane formed. This correlation between membrane thickness and duration of irradiation occurs because the photoinitiator diffuses at a steady rate, with diffusion being a continuously occurring process. Thus, the longer the duration of irradiation, the more photoinitiator will initiate polymerization in the macromer mix, the more macromer will polymerize, and the thicker the resulting membrane. Additional factors which affect membrane thickness are the number of reactive groups per macromer and the concentration of accelerators in the macromer solution. This technique allows the creation of very thin membranes because the photoinitiator is first present in a very thin layer at the surface of the biological material, and polymerization only occurs where the photoinitiator is present.

In the suspension polymerization method, a somewhat thicker membrane is formed than with the interfacial polymerization method, since in the suspension method polymerization occurs throughout the macromer solution. The thickness of membranes formed by the suspension method is determined in part by the viscosity of the macromer solution, the concentration of the macromer in that solution, the fluid mechanical environment of the suspension and surface active agents in the suspension. These membranes vary in thickness from between 50 and 300 microns.

Non-Biological Surfaces.

The macromer solution and initiator can also be applied to a non-biological surface intended to be placed in contact with a biological environment. Such surfaces include, for example, vascular grafts, contact lenses, intraocular lenses, ultrafiltration membranes, and containers for biological materials.

It is usually difficult to get good adhesion between polymers of greatly different physicochemical properties. The concept of a surface physical interpenetrating network was presented by Desai and Hubbel (N. P. Desai et al. (1992)). This approach to incorporating into the surface of one polymer a complete coating of a polymer of considerably different properties involved swelling the surface of the polymer to be modified (base polymer) in a mutual solvent, or a swelling solvent, for the base polymer and for the polymer to be incorporated (penetrant polymer). The penetrant polymer diffused into the surface of the base polymer. This interface was stabilized by rapidly precipitating or deswelling the surface by placing the base polymer in a nonsolvent bath. This resulted in entanglement of the penetrant polymer within the matrix of the base polymer at its surface in a structure that was called a surface physical interpenetrating network.

This approach can be improved upon by photopolymerizing the penetrant polymer upon the surface of the base polymer in the swollen state. This results in much enhanced stability over that of the previous approach and in the enhancement of biological responses to these materials. The penetrant may be chemically modified to be a prepolymer macromer, i.e. capable of being polymerized itself. This polymerization can be initiated thermally or by exposure to visible, ultraviolet, infrared, gamma ray, or electron beam irradiation, or to plasma conditions. In the case of the relatively nonspecific gamma ray or electron beam radiation reaction, chemical incorporation of particularly reactive sites may not be necessary.

Polyethylene glycol (PEG) is a particularly useful penetrant polymer for biomedical applications where the lack of cell adhesion is desired. The previous work had demonstrated an optimal performance at a molecular weight of 18,500 D without chemical crosslinking. PEG prepolymers can be readily formed by acrylation of the hydroxyl groups at its termini or elsewhere within the chain. These prepolymers can be readily polymerized. Photoinitiated polymerization of these prepolymers is particularly convenient and rapid. There are a variety of visible light initiated and ultraviolet light initiated reactions that are initiated by light absorption by specific photochemically reactive dyes. This same approach can be used with other water-soluble polymers, such as poly(N-vinyl pyrrolidinone), poly(N-isopropyl acrylamide), poly(ethyl oxazoline) and many others.

Method for Formation of Polymeric Materials.

Polymeric objects are formed into a desired shape by standard techniques known to those skilled in the art, where the macromer solution, preferably containing catalyst and initiator, is shaped, then polymerized. For example, slabs may be formed by casting on a flat surface and discoidal shapes by casting into discoidal containers. Cylinders and tubes can be formed by extrusion. Spheres can be formed from emulsion oil, by co-extrusion with oil, or by co-extrusion with air, another gas or vapor. The macromer is then exposed to conditions such as light irradiation, to initiate polymerization. Such irradiation may occur subsequent to, or, when desired, simultaneously with the shaping procedures.

The macromer may also be shaped in relationship to an internal or external supporting structure. Internal supporting structures include screening networks of stable or degradable polymers or nontoxic metals. External structures include, for example, casting the gel within a cylinder so that the internal surface of the cylinder is lined with the gel containing the biological materials.

Method for Surface Coating.

These materials can be applied to the treatment of macrocapsular surfaces, such as those used for ultrafiltration, hemodialysis and non-microencapsulated immunoisolation of animal tissue. The microcapsule in this case will usually be microporous with a molecular weight cutoff below 70,000 Da. It may be in the form of a hollow fiber, a spiral module, a flat sheet or other configuration. The surface of such a microcapsule can be modified using a polymer such as PEG to produce a non-fouling, non-thrombogenic, and non-cell-adhesive surface. The coating serves to enhance biocompatibility and to offer additional immunoprotection. Materials which can be modified in this manner include polysulfones, cellulosic membranes, polycarbonates, polyamides, polyimides, polybenzimidazoles, nylons, poly(acrylonitrile-co-vinyl chloride) copolymers, polyurethanes, polystyrene, poly(styrene co-acrylonitriles), poly(vinyl chloride), and poly(ethylene terephthalate).

A variety of methods can be employed to form biocompatible overcoats, depending on the physical and chemical nature of the surface. Hydrophilic surfaces can be coated by applying a thin layer (for example, between 50 and 300 microns in thickness) of a polymerizable solution such as PEG diacrylate containing appropriate amounts of dye and amine. Hydrophobic surfaces can be first rendered hydrophilic by gas plasma discharge treatment and the resulting surface can then be similarly coated, or they may simply be treated with a surfactant before or during treatment with the PEG diacrylate solution. For example, a hydrophobic polystyrene surface could first be treated by exposure to an $O_2$ plasma or an $N_2$ plasma. This results in rendering the surface more hydrophilic by the creation of oxygen-containing or nitrogen containing surface species, respectively. These species could be further treated by reaction with a substance such as acryloyl chloride, capable of producing surface-bound free radical sensitive species. Alteratively, a hydrophobic polystyrene surface could first be treated with a surfactant, such as a poly(ethylene oxide)-poly(propylene oxide) block copolymer, which could subsequently be acrylated if desired. Such treatments would result in enhanced adhesion between the hydrophilic coating layers and the hydrophobic material being treated.

Treatment of Textured Materials and Hydrogels.

The surface of materials having a certain degree of surface texture, such as woven dacron, dacron velour, and expanded poly(tetrafluoro-ethylene) (ePTFE) membranes, can be treated with the hydrogel. Textured and macroporous surfaces allow greater adhesion of the PEG gel to the material surface, allowing the coating of relatively hydrophobic materials such as PTFE and poly(ethylene terephalate) (PET).

Implantable materials such as enzymatic and ion sensitive electrodes, having a hydrogel (such as poly(HEMA), crosslinked poly(vinyl alcohol) and poly(vinyl pyrrolidone)), on their surface, are coated with the more biocompatible PEO gel in a manner similar to the dye adsorption and polymerization technique used for the alginate-PLL microspheres in the following examples.

Treatment of Dense Materials.

Gen coatings can be applied to the surfaces of dense (e.g., nontextured, nongel) materials such as polymers, including PET, PTFE, polycarbonates, polyamides, polysulfones, polyurethanes, polyethylene, polypropylene, polystyrene, glass, and ceramics. Hydrophobic surfaces are initially treated by a gas plasma discharge or surfactant to render the surface hydrophilic. This ensures better adhesion of the gel coating to the surface. Alternatively, coupling agents may be used to increase adhesion, as readily apparent to those skilled in the art of polymer synthesis and surface modification.

Thin Interfacially Polymerized Coatings Within Blood Vessels and Upon Other Tissues.

The methodology described above can also be used to photopolymerize very thin films of non-degradable polymer coatings with blood vessels to alter the interaction of blood platelets with the vessel wall and to deliver therapeutics such as enzymes and other proteins, polysaccharides such as hyaluronic acid, nucleic acids such as antisense and ribozymes, and other organic and inorganic drugs, using the methods described above.

The immediate effect of the polymerization of the polymer inside blood vessels is to reduce the thrombogenicity of an injured blood vessel surface. This has clear utility in improving the outcome of balloon angioplasty by reducing the thrombogenicity of the vessel and reducing the incidence of lesions created by balloon dilatation. Another effect of this modification may be to reduce smooth muscle cell hyperplasia. This is expected for two reasons. First, platelets contain a potent growth factor, platelet-derived growth factor (PDGF), thought to be involved in post-angioplasty hyperplasia. The interruption of the delivery of PDGF itself poses a pharmacological intervention, in that a "drug" that would have been delivered by the platelets would be prevented from being delivered. Thrombosis results in the generation of thrombin, which is a known smooth muscle cell mitogen. The interruption of thrombin generation and delivery to the vessel wall also poses a pharmacological intervention. Moreover, there are other growth factors soluble in plasma which are known to be smooth muscle cell mitogens. The gel layer presents a permselective barrier on the surface of the tissue, and thus the gel layer is expected to reduce hyperplasia after angioplasty. Further, the gel may reduce vasospasm by protecting the vessel from exposure to vasoconstrictors such as thrombin and may reduce the incidence of acute reclosure.

The restriction of the polymerization at an interface is a very important advantage. Disease lesions inside a blood vessel are highly irregular in shape. Thus, it is very difficult to use a preshaped object, such as a balloon, to make a form which is to contain the polymerizing material adjacent to the blood vessel.

There are several other organs where one needs to control cell interaction with tissues or to create similar barriers by bulk or interfacial polymerization. This methodology is equally applicable to the other organs, as well as to encapsulation of specific cell types or biologically active materials such as enzymes for treatment of various metabolic defects and diseases, for example, as described below.

(i) Encapsulation of Neurotransmitter-Releasing cells.

Paralysis agitans, more commonly called Parkinson's disease, is characterized by a lack of the neurotransmitter dopamine within the striatum of the brain. Dopamine secreting cells such as cells from the ventral mesencephalon, from neuroblastoid cell lines or from the adrenal medulla can be encapsulated using the method and materials described herein. Cells, including genetically engineered cells, secreting a precursor for a neurotransmitter, an agonist, a derivative or a mimic of a particular neurotransmitter or analogs can also be encapsulated.

(ii) Encapsulation of Hemoglobin for Synthetic Erythrocytes

Hemoglobin in its free form can be encapsulated in PEG gels and retained by selection of a PEG chain length and cross-link density which prevents diffusion. The diffusion of hemoglobin from the gels may be further impeded by the use of polyhemoglobin, which is a cross-linked form of hemoglobin. The polyhemoglobin molecule is too large to diffuse from the PEG gel. Suitable encapsulation of either native or crosslinked hemoglobin may be used to manufacture synthetic erythrocytes. The entrapment of hemoglobin in small spheres of less than 5 microns in diameter of these highly biocompatible materials would lead to enhanced circulation times relative to crosslinked hemoglobin or liposome encapsulated hemoglobin.

(iii) Entrapment of Enzymes for correction of Metabolic Disorders and Chemotherapy.

There are many diseases and defects which result from a deficiency in enzymes. For example, congenital deficiency of the enzyme catalase causes acatalasemia. Immobilization of catalase in PEG gel networks could provide a method of enzyme replacement to treat this disease. Entrapment of glucosidase can similarly be useful in treating Gaucher's disease. Microspherical PEG gels entrapping urease can be used in extracorporeal blood to convert urea into ammonia. Enzymes such as asparaginase can degrade amino acids needed by tumor cells. Immunogenicity of these enzymes prevents direct use for chemotherapy. Entrapment of such enzymes in immunoprotective PEG gels, however, can support successful chemotherapy. A suitable formulation can be designed for either slow release or no release of the enzyme.

(iv) Cellular Microencapsulation for Evaluation of Anti-Human Immunodeficiency Virus Drugs In Vivo HIV infected or uninfected human T-lymphoblastoid cells can be encapsulated into PEG gels as described for other cells above. These microcapsules can be implanted in a nonhuman animal and then treated with test drugs. After treatment, the microcapsules can be harvested and the encapsulated cells screened for viability and functional normalcy. Survival of infected T cells indicates successful action of the drug. Lack of biocompatibility is a documented problem in this approach to drug evaluations, but the highly biocompatible gels described herein should solve this problem.

(v) Polymerization of Structural Coatings within Blood Vessels and Other Tissue Lumens.

Just as very thin intravascular coatings can be polymerized within blood vessels, thicker layers of structural gels may also be polymerized within vessels. These may be used to reduce abrupt reclosure, to hold back vessel wall disections, to resist vasospasm, or to reduce smooth muscle cell hyperplasia. These gels may be produced by bulk or interfacial polymerization, and the thicker and higher the crosslink density of the material, the stronger the structure within the vessel wall. This procedure could be carried out upon or within many organs of the body.

The following examples are presented to describe preferred embodiments and utilities of the present invention and are not meant to limit the invention unless otherwise stated in the claims appended hereto. Taken together, the examples illustrate representative demonstrations of the best mode of implementing the invention as currently understood.

EXAMPLE 1

Synthesis of PEG 6 K Diacrylate.

PEG acrylates of molecular weights 400 Da and 1,000 Da are commercially available from Sartomer and Dajac Inc., respectively. 20 g of PEG 6K diol was dissolved in 200 ml dichloromethane in a 250 ml round bottom flask. The flask was cooled to 0° C. and 1.44 ml of triethyl amine and 1.3 ml of acryloyl chloride were added with constant stirring under a dry nitrogen atmosphere. The reaction mixture was then brought to room temperature and was stirred for 12 hr under a nitrogen atmosphere. It was then filtered, and the filtrate was precipitated by adding to a large excess of hexane. The crude monomer was purified by dissolving in dichloromethane and precipitating in hexane. Yield 60%.

EXAMPLE 2

Synthesis of PEG 18.5 K Tetraacrylate.

30 g of a tetrahydroxy water soluble PEG (mol wt 18,500) (PEG 18.5 k) was purchased from Polysciences, Inc.

The PEG was dried by dissolving in benzene and distilling off the water-benzene azeotrope. 59 g of PEG 18.5 k was dissolved in 300 ml of benzene in a 500 ml flask. To this, 3.6 ml of triethylamine and 2.2 ml of acryloyl chloride were added under nitrogen atmosphere and the reaction mixture was refluxed for 2 hours. It was then cooled and stirred overnight. The triethyl amine hydrochloride was separated by filtration and the copolymer was recovered from filtrate by precipitating in a large excess of hexane. The polymer was further purified by dissolving in methylene chloride and reprecipitating in hexane. The polymer was dried at 50° C. under vacuum for 1 day. Yield 68%.

EXAMPLE 3
Coating of Islet-Containing Alginate-PLL Microspheres by Surface Dye Adsorption.

The microcapsule interfacial polymerization method was used to form membrane around alginate-PLL microcapsules containing islets. Alginate-PLL coacervated microspheres, containing one or two human pancreatic islets each, were suspended in a 1.1% $CaCl_2$ solution and aspirated free of excess solution to obtain a dense plug of microspheres. A solution of ethyl eosin (0.04% w/v) was prepared in a 1.1% $CaCl_2$ solution. This solution was filter-sterilized by passage through a 0.45 μm filter. The plug of microspheres was suspended in 10 ml of the eosin solution for 2 min to allow uptake of the dye. The microspheres were then washed four times with fresh 1.1% $CaCl_2$ to remove excess dye. 2 ml of a solution (23% w/v) of PEG 18.5 tetraacrylate containing 100 μl of a 3.5% w/v solution of triethanolamine in hydroxyethylpiperazine ethanesulfonic acid (HEPES) buffered saline was added to 0.5 ml of these microspheres. The microbpheres were exposed to argon ion laser light for 30 seconds with periodic agitation. The suspension of microspheres was uniformly scanned with the light during this period. The microspheres were then washed with calcium solution and the process was repeated in order to further stabilize the coating.

A static glucose stimulation test (SGS) was performed on islets-encapsulated in the microspheres coated with PEG gel. Data for insulin secretion in response to this challenge appears in Table 1. The islets are seen to be viable by dithizone staining. The SGS test data confirm the vitality and functionality of the islets.

TABLE 1

Function of Encapsulated Islet Cells SGS
Glucose Concentration (mg %)

|  | Initial 60 | 300 | Subsequent 60 |
|---|---|---|---|
|  | Insulin/Islet/hr (μU/ml)* | | |
| Diffusion Overcoat Method | 1.0 | 10.04 ± 3.56 | 2.54 ± 0.76 |
| Mineral Oil Overcoat Method | 1.0 | 10.23 ± 3.28 | 1.02 ± 0.78 |
| Free Islet Control | 1.0 | 3.74 ± 1.4 | 1.9 ± 0.17 |

*Values are mean ± S.D., all are normalized as compared to the initial 60 mg %, after subjection to the 300 mg % glucose, the islets are resubjected to the initial dose.

PEG diacrylate macromers can be polymerized identically as the PEG tetraacrylate macromer described in this example.

EXAMPLE 4
Coating Islet-Containing Alginate-PLL Microspheres Suspension Polymerization Method This method takes advantage of the hydrophilic nature of PEG monomers. 2 ml of alginate/PLL microspheres, containing one or two human pancreatic islets each, were mixed with PEG tetraacrylate macromer solution (PEG mol wt 18.5 kD, 23% solution in saline) in a 50 ml transparent centrifuge tube. Triethanolamine (0.1 M) and 0.5 mM ethyl eosin were mixed with macromer solution. The excess macromer solution was decanted, 20 ml of mineral oil was added to the tube, and the reaction mixture was vortexed thoroughly for 5 minutes. Silicone oil will perform equally well in this synthesis but may have poorer adjuvant characteristics if there is any carry-over. Any other water-immiscible liquid may be used as the "oil" phase. Acceptable triethanolamine concentrations range from about 1 mM to about 100 mM. Acceptable ethyl eosin concentrations range from about 0.01 mM to more than 10 mM.

The beads were slightly red due to the thin coating of macromer/dye solution and were irradiated for 20–50 sec with an argon ion laser (power 50–500 mW). Bleaching of the (red) ethyl eosin color suggests completion of the reaction. The beads were then separated from the mineral oil and washed several times with saline solution. The entire procedure was carried out under sterile conditions.

Figure 3:
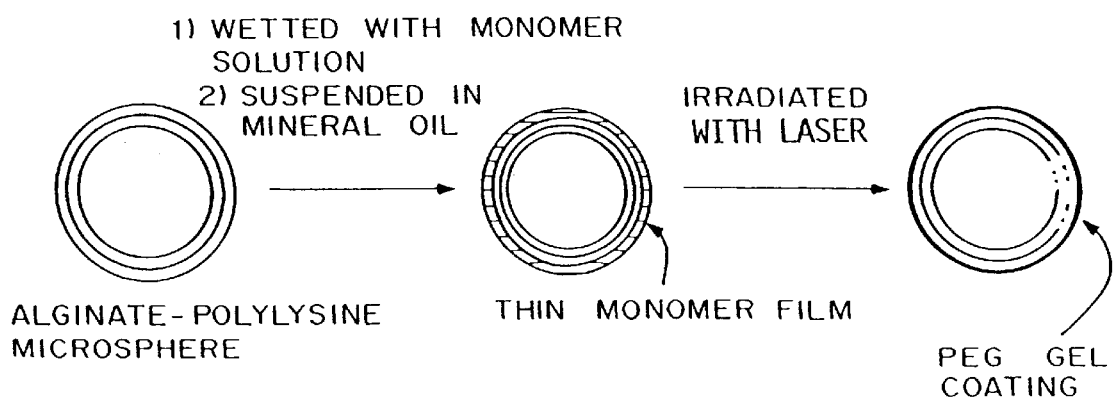
FIG. 3 is a schematic of photopolymerization of a PEG coating on alginate-poly(L-lysine) microspheres suspended in mineral oil.

A schematic representation of the macrosphere coating process in oil is shown in FIG. 3. Alginate/polylysine capsules are soluble in sodium citrate at pH 12. When these coated microspheres come in contact with sodium citrate at pH 12, the inner alainate/polylysine coacervate dissolves and a PEG polymeric membrane can still be seen (crosslinked PEG gels are substantially insoluble in all solvents including water and sodium citrate at pH 12). The uncoated control microspheres dissolve completely and rapidly in the same solution.

A static glucose challenge was performed on the islets as in Example 3. Data are also shown in Table 1. The islets are viable and functional.

EXAMPLE 5
Encapsulation of Islets of Langerhans

This example makes use of the direct interfacial polymerization. Islets of Langerhans isolated from a human pancreas were encapsulated in PEG tetraacrylate macromer gels. 500 islets suspended in RPMI 1640 medium containing 10% fetal bovine serum were pelleted by centrifuging at 100 g for 3 min. The pellet was resuspended in 1 ml of a 23% w/v solution of PEG 18.5 K tetraacrylate macromer in HEPES buffered saline. 5 μl of an ethyl eosin solution in vinyl pyrrolidone (at a concentration of 0.5%) was added to this solution along with 100 μl of a 5 M solution of triethanolamine in saline. 20 ml of a mineral oil was then added to the tube which was vigorously agitated to form a dispersion of droplets 200–500 μm in size. This dispersion was then exposed to an argon ion laser with a power of 250 mW, emitting at 514 nm, for 30 sec. The mineral oil was then separated by allowing the microspheres to settle, and the resulting microspheres were washed twice with phosphate buffered saline (PBS), once with hexane and three times with media.

The viaility of Islets of Langerhans encapsulated in a PEG-tetraacrylate gel was verified by an acridine orange and propidium iodide staining method and also by dithizone staining. In order to test functional normalcy, a SGS test was performed on these islets. The response of the encapsulated islets was compared to that of free islets maintained in culture for the same time period. All islets were maintained in culture for a week before the SGS was performed. The results are summarized in Table 2. It can be seen that the encapsulated islets secreted significantly ($p<0.05$) higher amounts of insulin than the free islets. The PEG-tetraacrylate gel encapsulation process did not impair function of the islets and in fact helped them maintain their function in culture better than if they had not been encapsulated.

TABLE 2

Secretion of Insulin from Islet Cells
Islet Insulin Secretion

|  | Glucose Concentration (mg %) | | |
| --- | --- | --- | --- |
|  | 60 | 300 | 60 |
|  | Insulin/islet/hr ($\mu$U/ml)* | | |
| Free islets | 1.0 | 3.74 ± 1.40 | 1.9 ± 0.17 |
| Encapsulated Islets | 1.0 | 20.81 ± 9.36 | 2.0 ± 0.76 |

*Values are mean ± S.D., normalized to initial basal level at 60 mg % glucose.

EXAMPLE 6
Microencapsulation of Animal Cells.

Figure 4:
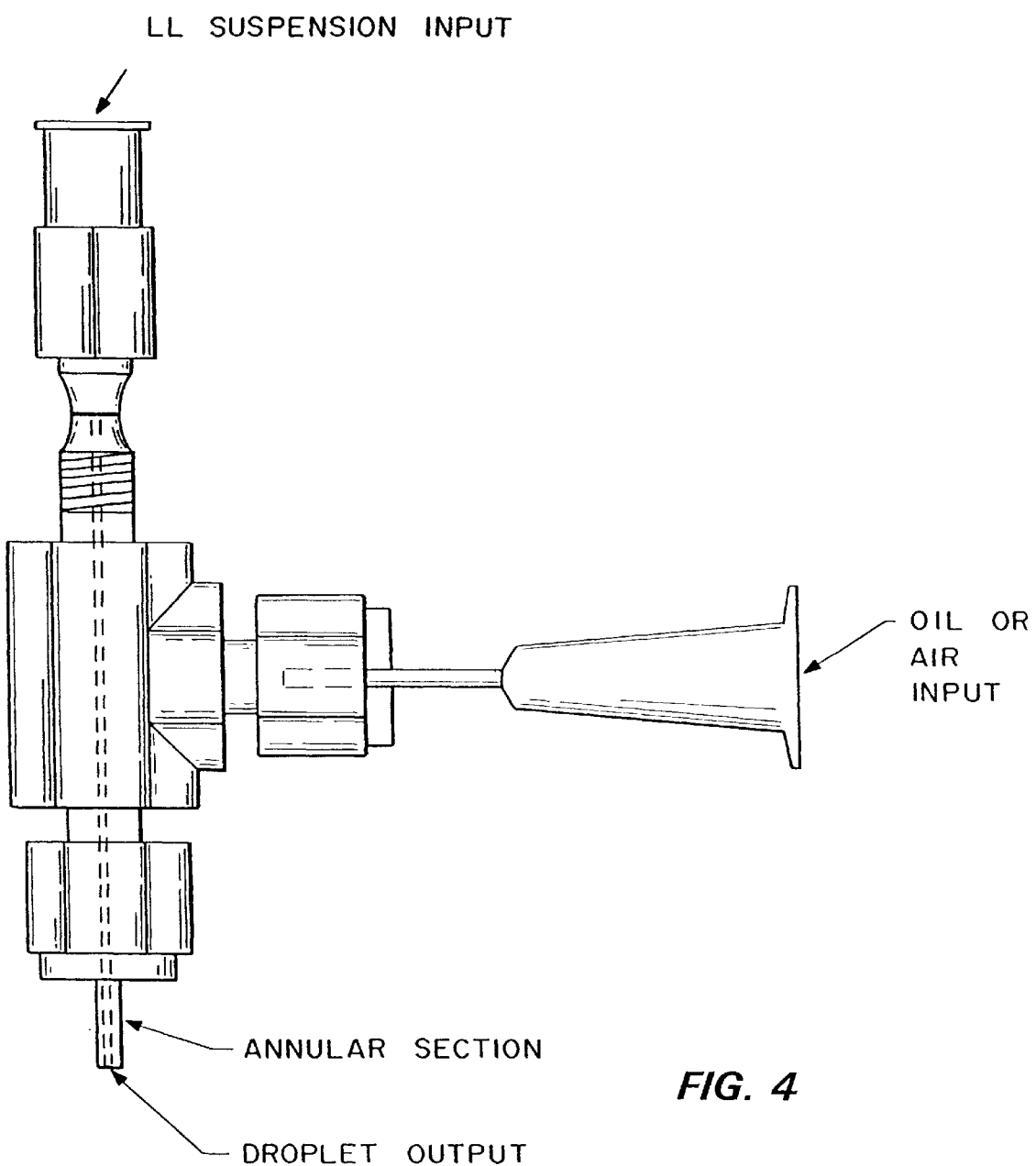
FIG. 4 is a schematic representation of coextrusion apparatus used for microencapsulation using laser polymerization

PEG diacrylates of different molecular weight were synthesized by a reaction of acryloyl chloride with PEG as in Example 1. A 20 to 30% solution of macromer was mixed with a cell suspension and the ethyl eosin and triethanolamine initiating system before exposing it to laser light through a coextrusion air flow apparatus shown in FIG. 4. Microspheres were prepared by an air atomization process in which a stream of macromer was atomized by an annular stream of air. The air flow rate used was 1,600 cc/min and macromer flow rate was 0.5 ml/min. The droplets were allowed to fall into a petri dish containing mineral oil and were exposed to laser light for about 0.15 sec each to polymerize the microspheres and make them insoluble in water. The microspheres were separated from the oil and thoroughly washed with PBS buffer to remove unreacted macromer and residual initiator. The size and shape of the microspheres was dependent on extrusion rate (0.05 to 0.1 ml/min) and extruding capillary diameter (18 Ga to 25 Ga). The polymerization times were dependent on initiator concentration (ethyl eosin concentration (5 $\mu$M to 0.5 mM), vinyl pyrrolidone concentration (0.0% to 0.1%), triethanolamine concentration (5 to 100 mM), laser power (10 mW to 1 W), and macromer concentration (greater than 10% w/v).

A PEG diacrylate macromer of molecular weight 400 Da was used as a 30% solution in PBS, containing 0.1 M triethanolamine as a cocatalyst and 0.5 mM ethyl eosin as a photoinitiator. The polymerizations were carried out at physiological pH in the presence of air. This is significant since radical polymerizations may be affected by the presence of oxygen, and the acrylate polymerization is still rapid enough to proceed effectively.

The process also works at lower temperatures. For cellular encapsulation, a 23% solution of PEG diacrylate was used with initiating and polymerization conditions as used in the air atomization technique. Cell viability subsequent to encapsulation was checked with the trypan blue exclusion assay. Human foreskin fibroblasts (HFF), Chinese hamster ovary cells (CHO-K1), and a beta cell insuloma line (RiN5F) were found to be viable (more than 95%) after encapsulation. A wide range of PEG diacrylate concentrations greater than 10% can be used equally effectively, as can PEG tetraacrylate macromers.

EXAMPLE 7
coating of Animal Cell-Containing Alginate-PLL Microspheres and Individual Cells by Surface Dye Adsorption.

Alginate-PLL coacervated microspheres containing animal cells were suspended in a 1.1% $CaCl_2$ solution and were aspirated free of excess solution to obtain a dense plug of microspheres. The plug of microspheres was suspended in 10 ml of eosin solution for 2 min to allow dye uptake. 2 ml of a solution (23% w/v) of PEG 18.5 tetraacrylate containing 100 Al of a 3.5 w/v solution of triethanolamine in HEPES buffered saline was added to 0.5 ml of these microspheres. The microspheres were exposed to an argon ion laser for 30 seconds with periodic agitation. The suspension of microspheres was uniformly scanned with the laser during this period. The microspheres were then washed with calcium solution and the process was repeated once more in order to attain a stable coating.

In order to verify survival of cells after the overcoat process, cells in suspension without the alginate/PLL microcapsule were exposed to similar polymerization conditions. 1 ml of lymphoblastic leukemia cells (RAJI) ($5 \times 10^5$ cells) was centrifuged at 300 g for 3 min. 1 ml of a 0.04% filter sterilized ethyl eosin solution was phosphate buffered saline (PBS) is added and the pellet was resuspended. The cells were exposed to the dye for 1 min and washed twice with PBS and then pelleted. 10 $\mu$l of triethanolamine solution (0.1 M) was added to the pellet and the tube was vortexed to resuspend the cells. 0.5 ml of PEG 18.5 K tetraacrylate macromer was then mixed into this suspension and the resulting mixture exposed to an argon ion laser (514 nm, 50 mW) for 45 sec. The cells were then washed twice with 10 ml saline and once with media (RPMI 1640 with 10% FCS and 1% antibiotic, antimycotic). A thin membrane of PEG-tetraacrylate gel was observed forming around each individual cell.

No significant difference in viability was seen between the control population (93% viable) and the treated cells (95% viable) by trypan blue exclusion. An assay for cell viability and function was performed by adapting the MTT-Formazan assay for the RAJI cells. This assay indicates greater than 90% survival. Similar assays were performed with two other model cell lines. Chinese hamster ovary cells (CHO-K1) show no significant difference (p<0.05) in metabolic function as evaluated by the MTT-Formazan assay. 3T3 mouse fibroblasts also show no significant reduction (p>0.50) in metabolic activity.

EXAMPLE 8
Coating Animal Cell Containing Alginate-PLL Microsphere Suspension Polymerization Method.

Using the method described in Example 4, RAJI cells encapsulated in alginate-PLL microspheres were coated with a PEG 18.5 K tetraacrylate polymeric membrane. Viability of these cells was checked by trypan blue exclusion and found to be more than 95% viable.

EXAMPLE 9
Coating of Individual Islets of Langerhans by Surface Dye Adsorption.

Using the method described in Example 7, ethyl eosin was adsorbed to the surfaces of islets, a solution of the PEG macromer with triethanolamine was applied to the dye-coated cells, and the cells were exposed to light from an argon-ion laser to form a thick PEG polymeric membrane on the surface of the islets. Islet viability was demonstrated by lack of staining with propidium iodide.

EXAMPLE 10
Biocompatibility of PEG on Microspheres.

In vivo evaluation of the extent of inflammatory response to microspheres prepared in Examples 7 and 8 was carried out by implantation in the peritoneal cavity of mice. Approximately 0.5 ml of microspheres were suspended in 5 ml of sterile HEPES buffered saline. 2.5 ml of this suspension was injected into the peritoneal cavity of ICR male swiss white mice. The microspheres were recovered after 4 days by lavage of the peritoneal cavity with 5 ml of 10U heparin/ml PBS. The extent of cellular growth on the microspheres was visually inspected under a phase contrast microscope. The number of unattached cells present in the recovered lavage fluid was counted using a Coulter counter.

Photographs were taken of alginate-poly(L-lysine) microspheres recovered after 4 days, and similar spheres which had been coated with PEG gel by the dye diffusion process before implantation. As expected, bilayer alginate-polylysine capsules not containing an outer alginate layer were completely covered with cells due to the highly cell adhesive nature of the PLL surface, whereas the PEG coated microspheres were virtually free of adherent cells. Almost complete coverage of alginate-poly(L-lysine) was expected because polylysine has amino groups on the surface, and positively charged surface amines can interact with cell surface proteoglycans and support cell growth (Reuveny, et al., (1983) *Biotechnol. Bioeng.*, 25:469–480). The photographs strongly indicate that the highly charged and cell adhesive surface of PLL is covered by a stable layer of PEG gel. The integrity of the gel did not appear to be compromised.

The non-cell-adhesive-tendency of these microspheres was evaluated as a percentage of the total microsphere area which appears covered with cellular overgrowth. These results are summarized in Table 3.

TABLE 3

Microsphere Coverage with Cell Overgrowth Following Implantation Intraperitoneally for 4 Days.

| Composition of PEG gel | % Cell coverage |
| --- | --- |
| 18.5 K | <1 |
| 18.5 k 90%:0.4 k 10% | <1 |
| 18.5 k 50%:0.4 k 50% | <1 |
| 35 k 90%:0.4 k 10% | 5–7 |
| 35 k 50%:0.4 k 50% | <1 |
| Alginate-poly(L-lysine) | 60–80 |

Figure 5:
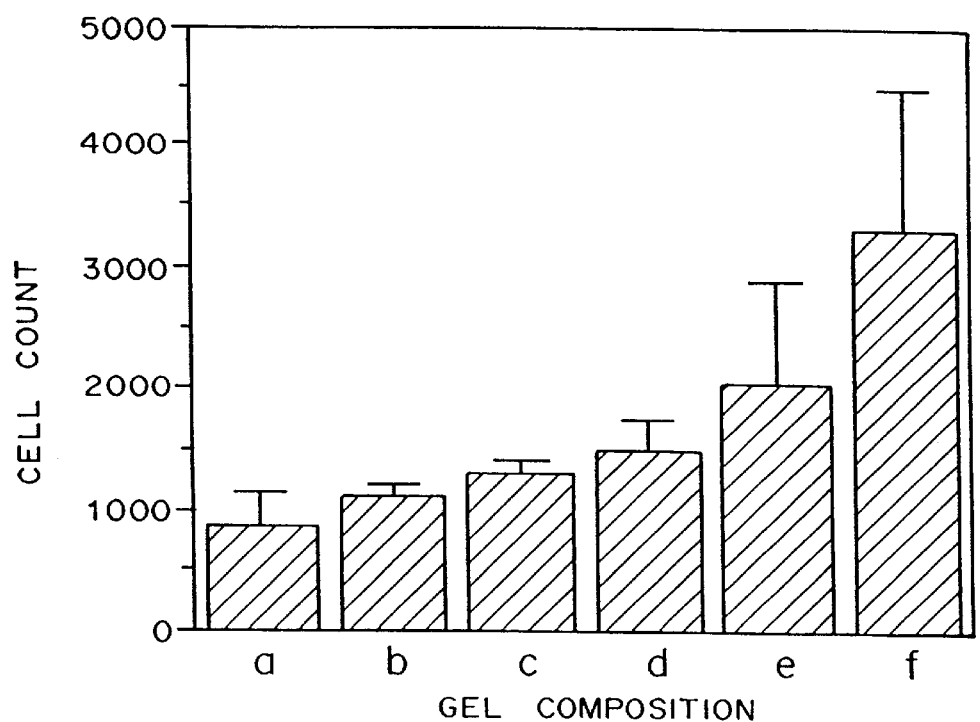
FIG. 5 is a graph of the number of cells versus gel composition, for the unattached cells obtained from lavage of the peritoneal cavity in mice with different PEO overcoat gel compositions: a—18.5 k; b—10% 0.5 k, 90% 18.5 k; c—50% 18.5 k, 50% 0.4 k; d—10% 0.4 k, 90% 35 k; e—50% 0.4k, 50% 35 k; and f—alginate-poly(L-lysine) control.

An increase in cell count is a result of activation of resident macrophages which secrete chemical factors such as interleukins and induce nonresident macrophages to migrate to the implant site. The factors also attract fibroblasts responsible. for collagen synthesis. The variation of cell counts with chemical composition of the overcoat is shown FIG. 5. It can be seen from the figure that all PEG coated spheres have substantially reduced cell counts. This is consistent with the PEG overcoat generally causing no irritation of the peritoneal cavity.

However, PEG composition does make a difference in biocompatibility, and increasing molecular weights are associated with a reduction in cell counts. This could be due to the gels made from higher molecular weight oligomers having higher potential for steric repulsion due to the longer chain lengths.

EXAMPLE 11
Permeability of PEG Gels.

Figure 6:
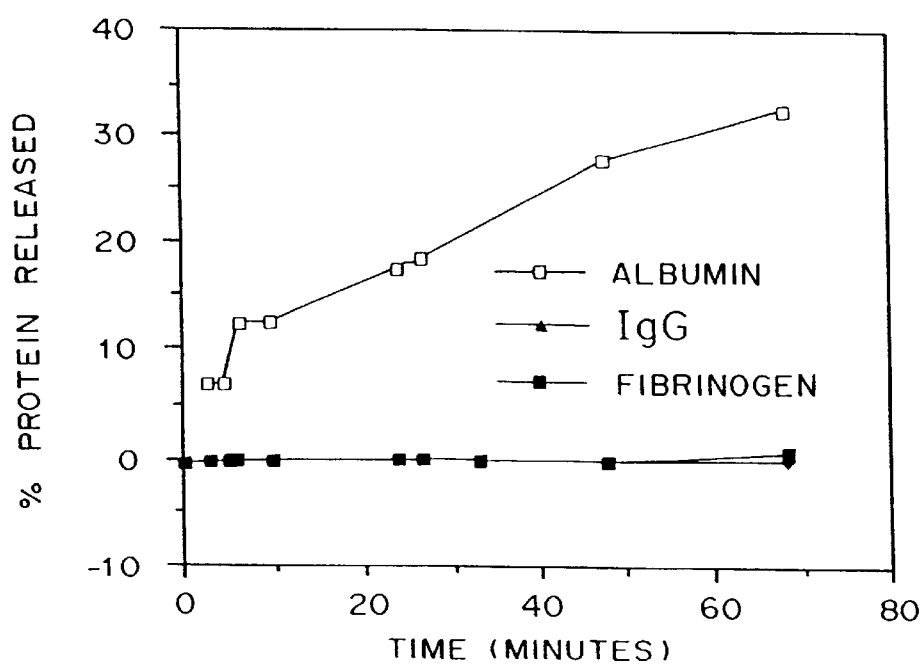
FIG. 6 is a graph of the % protein released versus time in minutes, for diffusion of bovine serum albumin (open squares), human IgG (triangles) and human fibrinogen (closed squares) through a PEO 18.5 K-tetraacrylate gel.

20 mg of bovine serum albumin, human IgG, or human fibrinogen was dissolved in 2 ml of a 23% w/v solution of oligomeric PEG 18.5 k tetraacrylate in PBS. This solution was laser polymerized to produce a gel 2 cm×2 cm×0.5 cm in size. The diffusion of bovine serum albumin, human IgG and human fibrinogen (mol wt 66 kDa, 150 kDa and 350 kDa respectively) was monitored through the 2 cm×2 cm face of these gels using a total protein assay reagent (Biorad). A typical release profile for a PEG 18.5 K gel was shown in FIG. 6. This gel allowed a slow transport of albumin but did not allow IgG and fibrinogen to diffuse. This indicates that these gels are capable of being used as immunoprotective barriers. This is a vital requirement for a successful animal tissue microencapsulation material.

Figure 7:
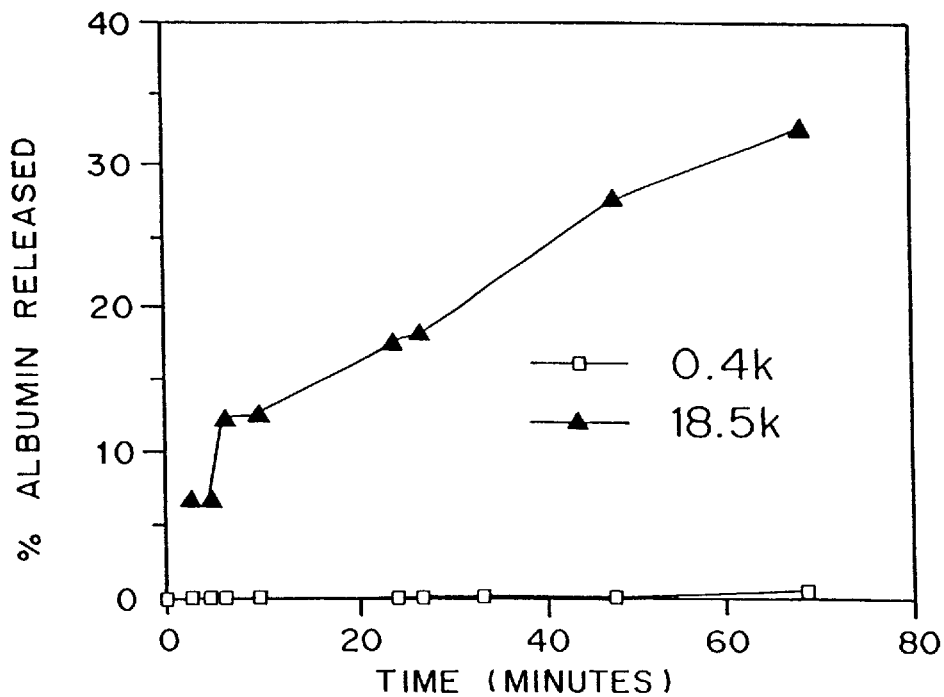
FIG. 7 is a graph of the % diffusion of bovine serum albumin over time in minutes through PEO 400 diacrylate (open squares) and PEG 18.5 K-tetracrylate (triangles) gels.

The release profile was found to be a function of crosslink density and molecular weight of the polyethylene glycol segment of the monomer. FIG. 7 shows the release of bovine serum albumin (BSA) through gels made from 23% solutions of PEO diacrylates and tetraacrylates of 0.4 K and 18.5 K, respectively. It is evident that the 18.5 K gel was freely permeable to albumin while the 0.4 K gel restricted the diffusion of albumin. The release of any substance from these gels depends on the crosslink density of the network and also depends on the motility of the PEG segments in the network. This effect was also dependent upon the functionality of the macromer. For example, the permeability of a PEG 18.5 K tetraacrylate gel was less than that of an otherwise similar PEG 20 K diacrylate gel.

EXAMPLE 12
Treatment of Silicone Rubber to form PEG Gel Layer to Enhance Biocompatibility.

2×2 cm pieces of medical grade silicone rubber were soaked for 1 h in benzene containing 23% 0.4 k PEG diacrylate and 0.5% 2,2-dimethoxy-2-phenyl acetophenone. The swollen rubber was irradiated for 15 min with a long wave UV lamp (365 nm). After irradiation, the sample was rinsed in benzene and dried. The air contact angles of silicone rubber under water were measured before and after treatment. The decreased contact angle of 500 after treatment, over the initial contact angle of 630 for untreated silicone rubber, reflects an increased hydrophilicity due to the presence of the PEG gel on the rubber surface.

This technique demonstrates that macromer polymerization can be used to modify a polymer surface so as to enhance biocompatibility. For instance, a polyurethane catheter can be treated by this method to obtain an implantable device coated with PEG. The PEG was firmly anchored anchored to the surface of the polyurethane catheter because the macromer was allowed to penetrate the catheter surface (to a depth of 1–2 microns) during the soaking period before photopolymerization. Upon irradiation, an interpenetrating network of PEG and polyurethane results. The PEG was thereby inextricably intertwined with the polyurethane.

EXAMPLE 13
Rate of Polymerization.

Figure 8:
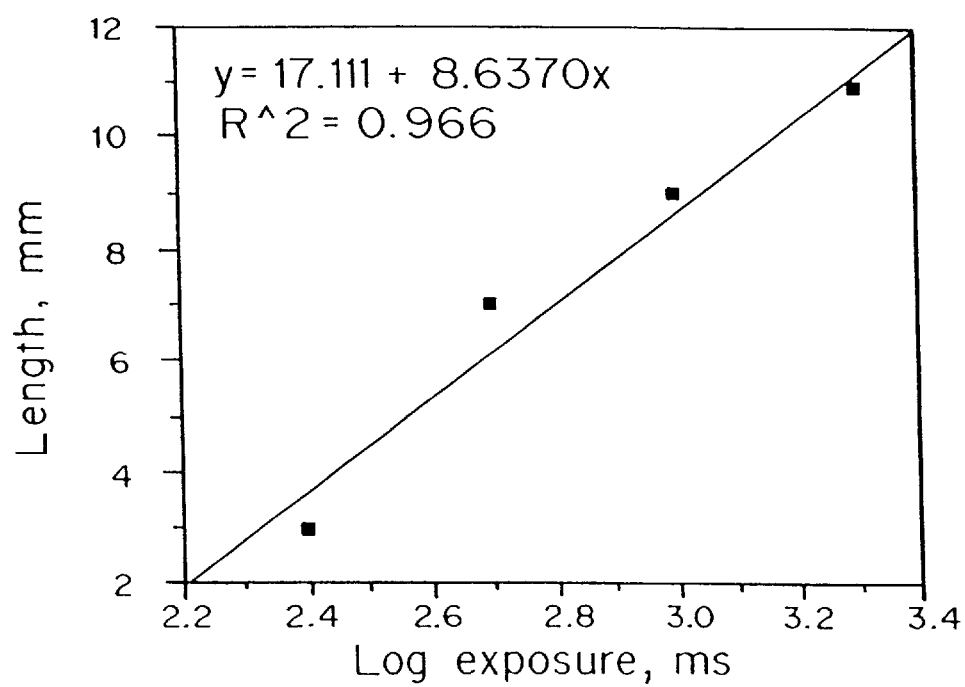
FIG. 8 is a graph of the length in mm of gel produced by argon ion laser induced polymerization versus log (time) (ms) of trimethylolpropane using an amine and ethyl eosin initiation system.

The kinetics of a typical reaction were determined to demonstrate rapidity of gelation in laser-initiated polymerizations of multifunctional acrylic monomers. Trimethylolpropyl-triacrylate, containing $5 \times 10^{-4}$ M ethyl eosin as a photoinitiator in 10 $\mu$moles of N-vinyl pyrrolidone per ml of macromer mix and 0.1 M of triethanolamine as a cocatalyst, was irradiated with a 500 mW argon ion laser (514 nm wavelength, power $3.05 \times 10^5$ W/m$^2$, beam diameter 1 mm, average gel diameter produced 1 mm). A plot of the length of the spike of gel formed by penetration of the laser beam into the gel versus laser irradiation time is shown in FIG. 8.

100 $\mu$l of a 23% w/w solution of various macromers in HEPES buffered saline containing 3 $\mu$l of initiator solution (300 mg/ml of 2,2 dimethoxy-2-phenoxyacetophenone in N-vinyl pyrrolidone) was placed on a glass coverslip and irradiated with a low intensity long wave UV (LWUV) lamp (Black-Ray, model 3-100A with flood). The times required for gelation to occur were noted and are given in Table 4. These times are typically in the range of 10 seconds.

TABLE 4

Gelling Times of Irradiated Polymer

| Polymer Size | Gel Time (sec) (mean ± S.D.) |
|---|---|
| 0.4 K | 6.9 ± 0.5 |
| 1 K | 21.3 ± 2.4 |
| 6 K | 14.2 ± 0.5 |
| 10 K | 8.3 ± 0.2 |
| 18.5 K | 6.9 ± 0.1 |
| 20 K | 9.0 ± 0.4 |

Time periods of about 10–100 ms are sufficient to gel a 300 μm diameter droplet, a typical size of gel used in microencapsulation technology. This rapid gelation, if used in conjunction with proper choice of macromers, can lead to entrapment of living cells in a three dimensional covalently bonded polymeric network. Monochromatic laser light will not be absorbed by the cells unless a proper chromophore is present, and is considered to be harmless if the wavelength is more than about 400 nm. Exposure to long wavelength ultraviolet light, greater than 360 nm, is harmless at practical intensities and durations.

The polymerization rate of the macromer will depend on the macromer concentration, the initiator concentration, and the functionality of the macromer, e.g., the difunctionality of a PEG diacrylate or the tetrafunctionality of a PEG tetraacrylate, as well as the degree of acrylation of the material.

EXAMPLE 14

PEG Gel Interactions.

Biocompatibility with HFF (human foreskin fibroblasts) cells was demonstrated as follows. HFF cells were seeded on PEG 18.5 K tetraacrylate gels at a density of 18,000 cells/cm$^2$ in Dulbecco's modification of Eagle's medium containing 10% fetal calf serum. The gels were then incubated at 37° C. in a 5% $CO_2$ environment for 4 hr. At the end of this time the gels were washed with PBS to remove any nonadherent cells and were observed under a phase contrast microscope at a magnification of 200X.

The growth of these cells on a typical PEG gel was as compared to the growth of these cells on a glass surface. The number of attached cells/cm$^2$ was found to be 510±170 on the gel surfaces as compared to 13,200±3,910 for a control glass surface. The cells on these gels appeared rounded and were not in their normal spread morphology, strongly indicating that these gels do not encourage cell attachment.

Biocompatibility on microspheres was demonstrated as follows. A photograph of microspheres explanted from mice as in Example 10 was taken; after 4 days very little fibrous overgrowth is seen. The resistance of PEG chains to protein adsorption and hence cellular growth is well documented. Table 5 summarizes the extent of cellular overgrowth seen on these microspheres formed of various PEG diacrylate gels after implanted intraperitoneally for four days.

TABLE 5

Extent of Cellular Overgrowth on Gels

| PEG Diacrylate for Gels (mol wt, Daltons) | Extent of Cellular Overgrowth |
|---|---|
| 400 | 5–10% |
| 1,000 | 15–25% |
| 5,000 | 3–5% |
| 6,000 | 2–15% |
| 10,000 | 10–20% |
| 18,500 | 4–10% |

EXAMPLE 15

Characterization and Mechanical Analysis of PEG Gels.

10 μl of an initiator solution containing 30 mg/ml of 2,2-dimethoxy-2-phenyl acetophenone in vinyl-2-pyrrolidone was added per ml to 23% w/v solutions of PEG diacrylates (0.4 K, 6 K, 10 K) and PEG tetraacrylates (18.5 K). The solution of initiator containing macromer was placed in a 4.0×1.0×0.5 cm mold and exposed to a long wave ultraviolet lamp (365 nm) for approximately 10 seconds to induce gelation. Samples were allowed to equilibrate in phosphate buffered saline (pH 7.4) for 1 week before analysis was performed.

A series of "dogbone" samples (samples cut from a slab into the shape of a dogbone, with wide regions at both ends and a narrower long region in the middle) were cut from ultimate tensile strength tests. Thickness of the samples was defined by the thickness of the sample from which they are cut. These thicknesses ranged from approximately 0.5 mm to 1.75 mm. The samples were 20 mm long and 2 mm wide at a narrow "neck" region. The stress strain tests were run in length control at a rate of 4% per second. After each test, the cross sectional area was determined. Table 6 shows the ultimate tensile strength data. It is seen that the lower molecular weight macromers in general give stronger gels which are less extensible than those made using the higher molecular weight macromers. The PEG 18.5 K tetraacrylate gel is seen to be anomalous in this series, resulting from the multifunctionality of the macromer and the corresponding higher crosslinking density in the resulting gel. This type of strengthening result could be similarly obtained with macromers obtained having other than four free radical-sensitive groups, such as acrylate groups.

TABLE 6

Gel Strength Tests

| | PEG Acrylate Precursor Molecular Weight | | | |
|---|---|---|---|---|
| | 0.4 K | 6 K | 10 K | 18.5 K |
| Stress (kpa)* | 168 +/− 51 | 98 +/− 15 | 33 +/− 7 | 115 +/− 56 |
| % Strain* | 8 +/− 3 | 71 +/− 13 | 110 +/− 9 | 40 +/− 15 |
| Slope* | 22 +/− 5 | 1.32 +/− 0.31 | 0.27 +/− 0.04 | 2.67 +/− 0.55 |

*Values are mean +/− S.D.

Figure 9A:
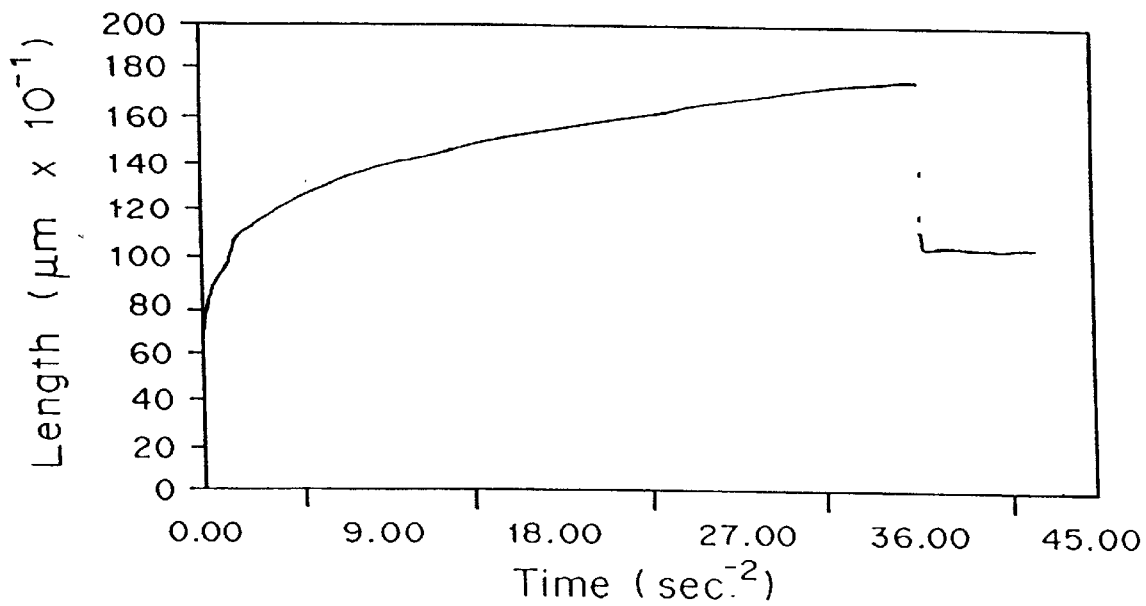
FIGS. 9A–C are creep curves for PEG diacrylate and tetraacrylate gels; test and recovery loads are given below the abscissa: A—1 k; B—6 K; and C—18.5 K PEG gels.
Figure 9B:
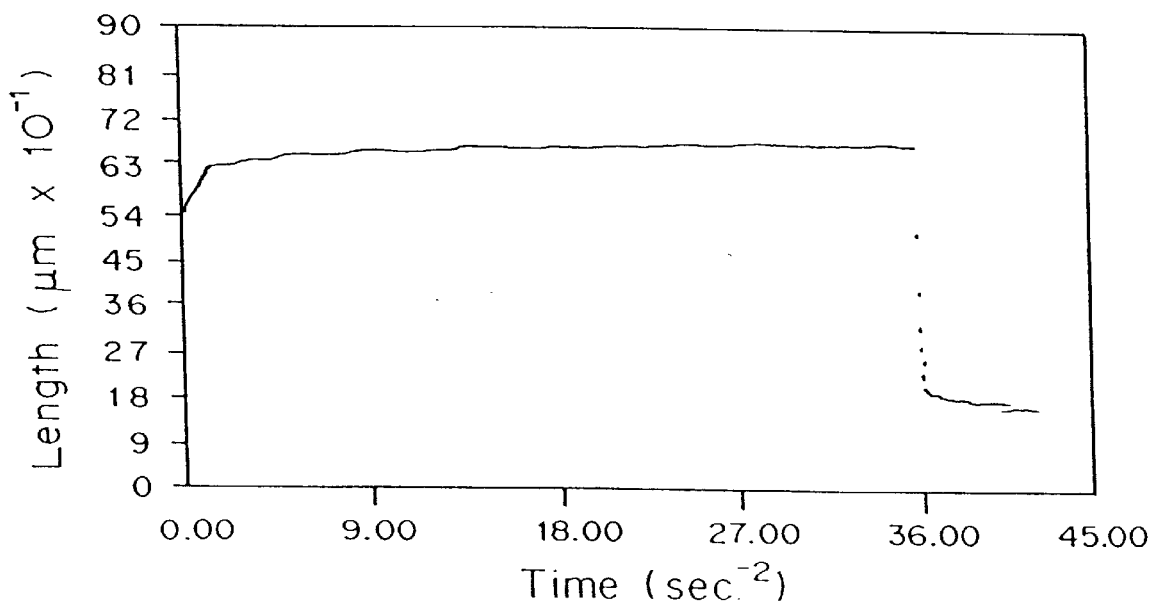
Figure 9C:
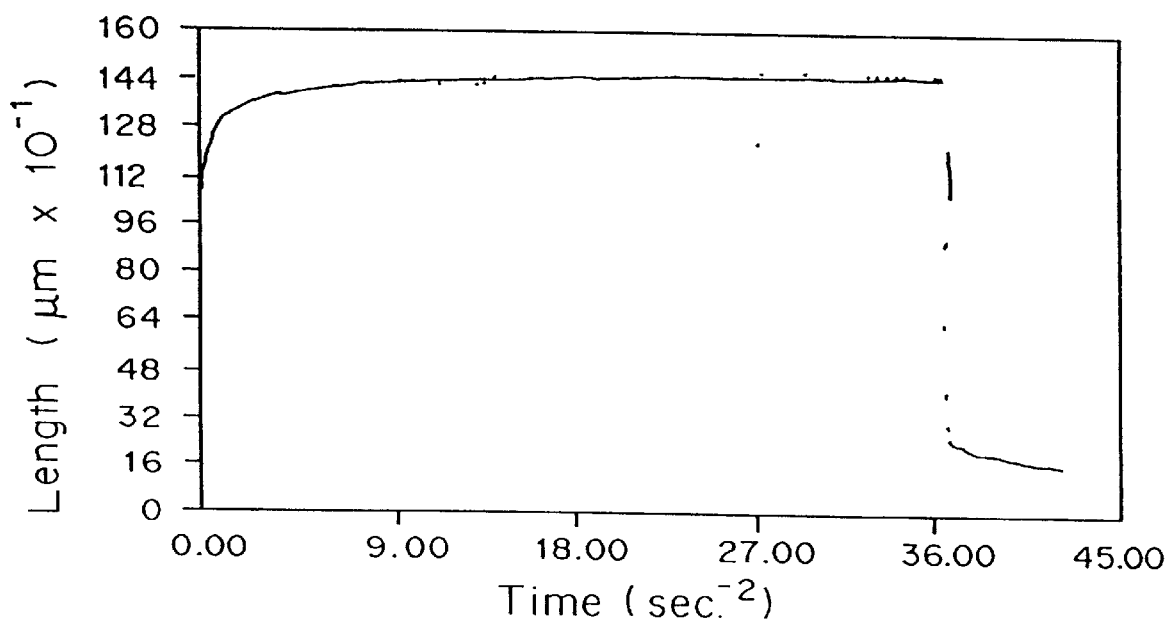

For the creep tests, eight samples approximately 0.2× 0.4×2 cm were loaded while submersed in saline solution. They were tested with a constant unique predetermined load for one hour and a small recovery load for ten minutes. Gels made from PEG diacrylates of 1 K, 6 K, and 10 K, and PEG tetraacrylates of 18.5 K PEG molecular weight were used for this study. The 10 K test was terminated due to a limit error (the sample stretched beyond the travel of the loading frame). The 1K sample was tested with a load of 10 g and a recovery load of 0.2 g. The 6 K sample was tested at a load of 13 g with a recovery load of 0.5 g. The 18.5 K sample was tested at a load of 13 g with a recovery load of 0.2 g. The choice of loads for these samples produced classical creep curves with primary and secondary regions. The traces for creep for the 1 K, 6 K, and 18.5 K samples appear in FIGS. 9A–C respectively.

EXAMPLE 16

Water Content of PEG Gels.

Solutions of various macromers were made as described above. Gels in the shape of discs were made using a mold. 400 μl of solution was used for each disc. The solutions were irradiated for 2 minutes to ensure thorough gelation. The disc shaped gels were removed and dried under vacuum at 60° C. for 2 days. The discs were weighed (W1) and then extracted repeatedly with chloroform for 1 day. The discs were dried again and weighed (W2). The gel fraction was calculated as W2/W1. This data appears in Table 7.

Subsequent to extraction, the discs were allowed to equilibrate with HBS for 6 hours and weighed (W3) after excess water had been carefully swabbed away. The total water content was calculated as (W3−W2)×100/W3. The data for gel water contents is summarized in the following table.

TABLE 7

Data for gel water contents.

| Polymer Code | % Total Water | % Gel Content |
|---|---|---|
| 0.4 | — | 99.8 ± 1.9 |
| 1 K | 79.8 ± 2.1 | 94.5 ± 2.0 |
| 6 k | 95.2 ± 2.5 | 69.4 ± 0.6 |
| 10 k | 91.4 ± 1.6 | 96.9 ± 1.5 |
| 18.5 k | 91.4 ± 0.9 | 80.3 ± 0.9 |
| 20 k | 94.4 ± 0.6 | 85.0 ± 0.4 |

EXAMPLE 17

Mechanical Stability of PEG Gels after Implantation.

PEG diacrylate (10 K) and PEG tetraacrylate (mol. wt. 18.5 k) were cast in dogbone shapes as described in Example 15. 23% w/w PEG-diacrylate or tetraacrylate in sterile HEPES buffered saline (HBS) (0.9% NaCl, 10 mM HEPES, pH 7.4), containing 900 ppm of 2,2-dimethoxy-2-phenoxyacetophenone as initiator, was poured into an aluminum mold and irradiated with a LWUV lamp (Black ray) for 1 min. The initial weights of these samples were found after oven-drying these gels to constant weight. The samples were Soxhlet-extracted with methylene chloride for 36 hours in order to leach out any unreacted prepolymer from the gel matrix (sol-leaching), prior to testing. The process of extraction was continued until the dried gels gave constant weight.

ICR Swiss male white mice, 6–8 weeks old (Sprague-Dawley), were anesthetized by an intraperitoneal injection of sodium pentobarbital. The abdominal region of the mouse was shaved and prepared with betadine. A ventral midline incision 10–15 mm long was made. The polymer sample, fully hydrated in sterile PBS (Phosphate buffered saline) or HEPES buffered saline (for calcification studies), was inserted through the incision and placed over the mesentery, away from the wound site. The peritoneal wall was closed with a lock stitched running suture (4.0 silk, Ethicon). The skin was closed with stainless steel skin staples, and a topical antibiotic (Furacin) was applied over the incision site. Three animals were used for each time point. One dogbone sample was implanted per mouse and explanted at the end of 1 week, 3 weeks, 6 weeks, and 8 weeks. Explanted gels were rinsed in HBS twice and then treated with 0.3 mg/ml pronase (Calbiochem) to remove any adherent cells and tissue. The samples were then oven-dried to a constant weight extracted and reswelled as mentioned before.

Tensile stress strain test was conducted on both control (unimplanted) and explanted dogbones in a small horizontal Instron-like device. The device is an aluminum platform consisting of two clamps mounted flat on a wooden board between two parallel aluminum guide. The top clamp is stationary while the bottom clamp is movable. Both the frictional surfaces of the moving clamp and the platform are coated with aluminum backed Teflon (Cole-Parmer) to minimize frictional resistance. The moving clamp is fastened to a device capable of applying a gradually increasing load. The whole set-up is placed horizontally under a dissecting microscope (Reichert) and the sample elongation is monitored using a video camera. The image from the camera is acquired by an image processor (Argus-10, Hamamatsu) and sent to a monitor. After breakage, a cross section of the break surface is cut and the area measured The load at break is divided by this cross section to find the maximum tensile stress. Table 8 lists the stress at fracture of PEG tetraacrylate (18.5 K) hydrogels explanted at various time intervals. No significant change in tensile strength is evident with time. Thus, the gels appear mechanically stable to biodegradation in vivo within the maximum time frame of implant in mice.

TABLE 9

Resistance to degradation of Polymer Implants

| TIME IMPLANTED | STRESS (KPa) (mean ± error*) | STRAIN AVE. (mean ± error*) |
|---|---|---|
| 1 WK | 52.8 ± 16.7 | 0.32 ± 0.19 |
| 3 WK | 36.7 ± 10.6 | 0.37 ± 0.17 |
| 6 WK | 73.3 ± 34.9 | 0.42 ± 0.26 |
| 8 WK | 34.1# | 0.30# |
| CONTROL | 44.9 ± 5.3 | 0.22 ± 0.22 |

*Error based on 90% confidence limits.
Single sample.

EXAMPLE 18

Monitoring of Calcification of PEG Gels.

Disc shaped PEG-tetraacrylate hydrogels (mol. wt. 18.5 k) were implanted intraperitoneally in mice as described above for a period of 1 week, 3 weeks, 6 weeks or 8 weeks. Explanted gels were rinsed in HBS twice and treated with Pronase (Calbiochem) to remove cells and cell debris. The samples were then equilibrated in HBS to let free $Ca^{++}$ diffuse out from the gel matrix. The gels were then oven-dried (Blue-M) to a constant weight and transferred to Aluminum oxide crucibles (COORS, high temperature resistant). They were incinerated in a furnace at 700° C. for at least 16 hours. Crucibles were checked for total incineration, if any residual remnants or debris was seen they were additionally incinerated for 12 hours. Subsequently, the crucibles were filled with 2 ml of 0.5 M HCl to dissolve $Ca^{++}$ salt and other minerals in the sample. This solution was filtered and analyzed with atomic absorption spectroscopy (AA) for calcium content.

Calcification data on PEG-tetraacrylate (mol. wt. 18.5 K) gel implants is given in Table 9. No significant increase in calcification was observed up to an 8 week period of implantation in mice.

TABLE 9

Calcification data on PEG-tetraacrylate (mol. wt. 18.5 K) gel implants

| TIME (Days) | CALCIFICATION (mean ± error*) (mg Calcium/g of Dry gel wt.) |
|---|---|
| 7 | 2.33 ± 0.20 |
| 21 | 0.88 ± 0.009 |
| 42 | 1.08 ± 0.30 |
| 56 | 1.17 ± 0.26 |

*Error based on 90% confidence limits.

EXAMPLE 19
Use of PEG Gels as Adhesive to Rejoin Severed Nerve.

A formulation of PEG tetraacrylate (10%, 18.5 K), was used as adhesive for stabilizing the sutureless apposition of the ends of transected sciatic nerves in the rat. Rats were under pentobarbital anesthesia during sterile surgical procedures. The sciatic nerve was exposed through a lateral approach by deflecting the heads of the biceps femoralis at the mid-thigh level. The sciatic nerve was mobilized for approximately 1 cm and transected with iridectomy scissors approximately 3 mm proximal to the tibial-peroneal bifurcation. The gap between the ends of the severed nerves was 2–3 mm. The wound was irrigated with saline and lightly swabbed to remove excess saline. Sterile, unpolymerzed PEG tetraacrylate solution was applied to the wound. Using delicate forceps to hold the adventitia or perineurium, the nerve ends were brought into apposition, the macromer solution containing 2,2-dimethoxy-2-phenoxyacetophenone. as a photoinitiator applied to the nerve ends and the wound was exposed to long wavelength UV-light (365 nm) for about 10 sec to polymerize the adhesive. The forceps were gently pulled away. Care was taken to prevent the macromer solution from flowing between the two nerve stumps. Alternatively, the nerve stump junction was shielded from illumination, e.g., with a metal foil, to prevent gelation of the macroner solution between the stumps; the remaining macromer solution was then simply washed away.

In an alternative approach, both ends of the transected nerve can be held together with one pair of forceps. Forceps tips are coated lightly with petrolatum to prevent reaction with the adhesive.

The polymerized adhesive serves to encapsulate the wound and adhere the nerve to the underlying muscle. The anastomosis of the nerve ends resists gentle mobilization of the joint, demonstrating a moderate degree of stabilization. The muscle and skin were closed with sutures. Re-examination after one month shows that severed nerves remain reconnected, despite unrestrained activity of the animals.

EXAMPLE 20
Surgical Adhesive.

Abdominal muscle flaps from female New Zealand white rabbits were excised and cut into strips 1 cm×5 cm. The flaps were approximately 0.5 to 0.8 cm thick. The lap joint, 1 cm×1 cm, was made using two such flaps. Two different PEO di- and tetra-acrylate macromer compositions, 0.4 K (di-) and 18.5 K (tetra-), were evaluated. The 0.4 K composition was a viscous liquid and was used without further dilution. The 18.5 K composition was used as a 23% w/w solution in HBS. 125 µl of ethyl eosin solution in n-vinyl pyrrolidone (20 mg/ml) along with 50 µl of triethanolamine was added to each ml of the adhesive solution. 100 µl of adhesive solution was applied to each of the overlapping flaps. The lap joint was then irradiated by scanning with a 2 W argon ion laser for 30 seconds from each side. The strength of the resulting joints was evaluated by measuring the force required to shear the lap joint. One end of the lap joint was clamped and an increasing load was applied to the other end, while holding the joint horizontally until it failed. Four joints were tested for each composition. The 0.4 K joints had a strength of 12.0±6.9 KPa (mean±S.D.), while the 18.5 K joints had a strength of 2.7±0.5 KPa. It is significant to note that it was possible to achieve photopolymerization and reasonable joint strength despite the 6–8 mm thickness of tissue. A spectrophotometric estimate using 514 nm light showed less than 1% transmission through such muscle tissue.

EXAMPLE 21
Modification of Polyvinyl Alcohol.

2 g of polyvinyl alcohol (mol wt 100,000–110,000) was dissolved in 20 ml of hot DMSO. The solution was cooled to room temperature and 0.2 ml of triethylamine and 0.2 ml of acryloyl chloride was added with vigorous stirring, under an argon atmosphere. The reaction mixture was heated to 70° C. for 2 hr and cooled. The polymer was precipitated in acetone, redissolved in hot water and precipitated again in acetone. Finally it was dried under vacuum for 12 hr at 60° C. 5–10% w/v solution of this polymer in PBS was mixed with the UV photoinitiator and polymerized using long wavelength UV light to make microspheres 200–1,000 microns in size.

These microspheres were stable to autoclaving in water, which indicates that the gel is covalently cross-linked. The gel is extremely elastic. This macromer, PVA multiacrylate, may be used to increase the crosslinking density in PEG diacrylate gels, with corresponding changes in mechanical and permeability properties. This approach could be pursued with any number of water-soluble polymers chemically modified with photopolymerizable groups, for example with water-soluble polymers chosen from polyvinylpyrrolidone, polyethyloxazoline, polyethyleneoxide-polypropyleneoxide copolymers, polysaccharides such as dextran, alginate, hyaluronic acid, chondroitin sulfate, heparin, heparin sulfate, heparan sulfate, guar gum, gellan gum, xanthan gum, carrageenan gum, and proteins, such as albumin, collagen, and gelatin.

EXAMPLE 22
Use of Alternative Photopolymerizable Moieties.

Many photopolymerizable groups may be used to enable gelation. To illustrate a typical alternative synthesis, a synthesis for PEG 1 K urethane methacrylate is described as follows:

In a 250 ml round bottom flask, 10 g of PEG 1 K diol was dissolved in 150 ml benzene. 3.38 g of 2-isocyanatoethylmethacrylate and 20 µl of dibutyltindilaurate were slowly introduced into the flask. The reaction was refluxed for 6 hours, cooled and poured into 1000 ml hexane. The precipitate was then filtered and dried under vacuum at 60° C. for 24 hours. In this case, a methacrylate free radical polymerizable group was attached to the polymer via a urethane linkage, rather than an ester link as is obtained, e.g. when reacting with aryloxyl chloride.

EXAMPLE 23
Formation of Alginate-PLL-alginate Microcapsules with Photopolymerizable Polycations.

Alginate-polylysine-alginate microcapsules are made by adsorbing, or coacervating, a polycation, such as polylysine (PLL), upon a gelled microsphere of alginate. The resulting membrane is held together by charge-charge interactions and thus has limited stability. To increase this stability, the polycation can be made photopolymerizable by the addition of a carbon-carbon double bond, for example. This can be used to increase the stability of the membrane by itself, or to react, for example, with photopolymerizable PEG to enhance biocompatibility.

To illustrate the synthesis of such a photopolymerizable polycation, 1 g of polyallylamine hydrochloride was weighed in loo ml glass beaker and dissolved in 10 ml distilled water (DW). The pH of the polymer solution was adjusted to 7 using 0.2 M sodium hydroxide solution. The polymer was then separated by precipitating in a large excess of acetone. It was then redissolved in 10 ml DW and the solution was transferred to 50 ml round bottom flask. 0.2 ml glycidyl methacrylate was slowly introduced into the reaction flask and the reaction mixture was stirred for 48 hours at room temperature. The solution was poured into 200 ml acetone and the precipitate was separated by filtration and dried in vacuum. This macromer is useful in photochemically stabilizing an alginate-PLL-alginate, both in the presence or in the absence of a second polymerizable species such as a PEG diacrylate.

In addition to use in encapsulating cells in materials such as alginate, such photopolymerizable polycations may be useful as a primer or coupling agent to increase polymer adhesion to cells, cell aggregates, tissues and synthetic materials, by virtue of adsorption of the photopolymerizable polymer bonding to the PEG photopolymerizable gel.

EXAMPLE 24
Encapsulation of Hemoglobin for Synthetic Erythrocytes.

Hemoglobin in its free form can be encapsulated in PEG gels and retained by selection of a PEG chain length and cross-link density which prevents diffusion. The diffusion of hemoglobin from the gels may be further impeded by the use of polyhemoglobin, which is a cross-linked form of hemoglobin. The polyhemoglobin molecule is too large to diffuse from the PEG gel. Suitable encapsulation of either native or crosslinked hemoglobin can be used to manufacture synthetic erythrocytes. The entrapment of hemoglobin in small spheres, less than five microns, of these highly biocompatible materials should lead to enhanced circulation times relative to crosslinked hemoglobin or liposome encapsulated hemoglobin.

Hemoglobin in PBS is mixed with the prepolymer in the following formulation:

| Hemoglobin at the desired amount | |
|---|---|
| PEG DA (MW 10000) | 35% |
| PEG DA (MW 1000) | 5% |
| PBS | 60% | with 2,2-dimethoxy, 2-phenyl acetophenone at 1.6% of the above solution.

This solution is placed in mineral oil at a ratio of 1 part hemoglobin/prepolymer solution to 5 parts mineral oil and is rapidly agitated with a motorized mixer to form an emulsion, which is then illuminated with a long-wavelength ultraviolet light (360 nm) for 5 min to crosslink the PEG prepolymer to form a gel. The molecular weight of the prepolymer can be selected to resist the diffusion of the hemoglobin from the gel, with smaller PEG molecular weights giving less diffusion. PEG DA of molecular weight 100,000, further crosslinked with PEG DA 1000, should possess the appropriate permselectivity to restrict hemoglobin diffusion, and it should possess the appropriate biocompatibility to circulate within the bloodstream.

EXAMPLE 25
Entrapment of Enzymes for Correction of Metabolic Disorders and Chemotherapy.

Congenital deficiency of the enzyme catalase causes acatalasemia. Immobilization of catalase in PEG gel networks could provide a method of enzyme replacement to treat this disease. Entrapment of glucosidase can similarly be useful in treating Gaucher's disease. Microspherical PEG gels entrapping urease can be used in extracorporeal blood to convert urea into ammonia. Enzymes such as asparaginase can degrade amino acids needed by tumor cells. Immunogenicity of these enzymes prevents direct use for chemotherapy. Entrapment of such enzymes in PEG gels, however, can support successful chemotherapy. A suitable formulation can be developed for either slow release or no release of the enzyme.

Catalase in PBS is mixed with the prepolymer in the following formulation:

| Catalase at the desired amount | |
|---|---|
| PEG DA (MW 10000) | 35% |
| PEG DA (MW 1000) | 5% |
| PBS | 60% | with 2,2-dimethoxy, 2-phenyl acetophenone at 1.6% of the above solution.

This solution is placed in mineral oil at a ratio of 1 part catalase/prepolymer solution to 5 parts mineral oil and is rapidly agitated with a motorized mixer to form an emulsion. This emulsion is illuminated with a long-wavelength ultraviolet light (360 nm) for 5 min to crosslink the PEG prepolymer to form a gel. The mw of the prepolymer may be selected to resist the diffusion of the catalase from the gel, with smaller PEG DA molecular weights giving less diffusion.

PEG DA of MW 10,000, further crosslinked with PEG DA 1000, should possess the appropriate permselectivity to restrict catalase diffusion, and it should possess the appropriate permselectivity to permit the diffusion of hydrogen peroxide into the gel-entrapped catalase to allow the enzymatic removal of the hydrogen peroxide from the bloodstream. Furthermore, it should possess the appropriate biocompatibility to circulate within the bloodstream.

In this way, the gel is used for the controlled containment of a bioactive agent within the body. The active agent (enzyme) is large and is retained within the gel, and the agent upon which it acts (substrate) is small and can diffuse into the enzyme rich compartment. However, the active agent is prohibited from leaving the body or targeted body compartment because it cannot diffuse out of the gel compartment.

EXAMPLE 26
Cellular Microencapsulation for Evaluation of Anti-Human Immunodeficiency Virus Drugs In Vivo.

HIV infected or uninfected human T-lymphoblastoid cells can be encapsulated into PEG gels as described for other cells above. These microcapsules can be implanted in a nonhuman animal to create a test sytem for anti-HIV drugs, and then treated with test drugs such as AZT or DDI. After treatment, the microcapsu-les can be harvested and the encapsulated cells screened for viability and functional normalcy using a fluorescein diacetate/ethidium bromide live/dead cell assay. Survival of infected cells indicates successful action of the drug. Lack of biocompatibility is a documented problem in this approach to drug evaluations, but can be overcome by using the gels described herein.

Modifications and variations are obvious from the foregoing detailed description. Such modifications and variations are intended to come within the scope of the following claims.

We claim:

1. A method for the treatment of a medical condition at a localized site, comprising the steps in the following order:

applying a polymerization initiator to the site;

applying a substantially water-soluble, degradable macromer of at least 200 mw to the site, wherein the macromer comprises at least two crosslinkable substituents, wherein at least one crosslinkable substituent can crosslink the macromer to other macromers under the influence of the initiator; and polymerizing the macromer to form a crosslinked polymeric material at the site;

wherein the crosslinked material assists in treatment of the medical condition.

2. The method of claim 1 wherein the initiator is a free-radical initiator, and the substituent is a free-radical polymerizable substituent.

3. The method of claim 1 wherein the initiator absorbs to a material at the site.

4. The method of claim 1 wherein excess or unabsorbed initiator is removed prior to application of macromer or is substantially diluted by application of initiator.

5. The method of claim 1 wherein the treatment comprises creating a barrier around a site selected from the group consisting of a tissue, an organ, a cell, and a cluster of cells.

6. The method of claim 5 wherein the barrier provides immunoisolation of the site.

7. The method of claim 5 wherein the barrier prevents the adhesion of the site to another surface.

8. The method of claim 7 wherein the barrier prevents post-surgical adhesions.

9. The method of claim 6 wherein the barrier prevents the adhesion of nerves.

10. The method of claim 5 wherein the barrier is applied to a blood vessel.

11. The method of claim 1 where the macromer is in a solution that further comprises a biologically active molecule.

12. The method of claim 11 wherein the crosslinked polymeric meterial provides controlled release of the biologically active molecule.

13. The method of claim 1 wherein at least some of the macromer is polycationic.

14. The method of claim 1 wherein the crosslinked polymeric material is formed on a surface of an implanted material.

15. The method of claim 14 wherein the implanted surface is a synthetic material.

16. The method of claim 14 wherein the surface is the surface of a capsule surrounding a tissue, an organ, a cell or a cluster of cells.

17. The method of claim 1 wherein the crosslinked polymeric material adheres two surfaces together.

* * * * *